US008034956B2

(12) United States Patent
Tsukada et al.

(10) Patent No.: US 8,034,956 B2
(45) Date of Patent: Oct. 11, 2011

(54) IONIC LIQUID AND METHOD FOR PRODUCING THE SAME, METHOD FOR FORMING OXIDE FILM ON METAL SURFACE, ELECTROLYTE CAPACITOR AND ELECTROLYTE

(75) Inventors: Yasuhiro Tsukada, Kobe (JP); Masamitsu Tachibana, Settsu (JP); Hiroyuki Furutani, Takatsuki (JP); Hideo Yamagishi, Kyotanabe (JP); Mutsuaki Murakami, Settsu (JP)

(73) Assignee: Kaneka Corporation, Osaka (JP)

( * ) Notice: Subject to any disclaimer, the term of this patent is extended or adjusted under 35 U.S.C. 154(b) by 286 days.

(21) Appl. No.: 11/667,541

(22) PCT Filed: Nov. 11, 2005

(86) PCT No.: PCT/JP2005/020705
§ 371 (c)(1),
(2), (4) Date: May 11, 2007

(87) PCT Pub. No.: WO2006/051897
PCT Pub. Date: May 18, 2006

(65) Prior Publication Data
US 2007/0263341 A1      Nov. 15, 2007

(30) Foreign Application Priority Data

Nov. 12, 2004   (JP) .................................. 2004-329424
Nov. 12, 2004   (JP) .................................. 2004-329715
Jun. 7, 2005   (JP) .................................. 2005-166602
Jun. 8, 2005   (JP) .................................. 2005-167883

(51) Int. Cl.
    *C07D 233/64*   (2006.01)
(52) U.S. Cl. .................................. 548/343.1
(58) Field of Classification Search .............. 548/343.1
    See application file for complete search history.

(56) References Cited

U.S. PATENT DOCUMENTS

| | | | |
|---|---|---|---|
| 3,563,999 A | 2/1971 | Anello et al. | |
| 4,049,668 A | 9/1977 | Szur | |
| 5,827,602 A * | 10/1998 | Koch et al. | 429/328 |
| 2003/0080312 A1 | 5/2003 | Seddon et al. | |
| 2004/0002002 A1 | 1/2004 | Mizuta et al. | |
| 2005/0175867 A1 | 8/2005 | Adachi et al. | |

FOREIGN PATENT DOCUMENTS

| | | | |
|---|---|---|---|
| EP | 1548750 A1 | | 6/2005 |
| JP | 2001-517205 A | | 10/2001 |
| JP | 2003-022938 A | | 1/2003 |
| JP | 2003-062467 | * | 3/2003 |
| JP | 2003-062467 A | | 3/2003 |
| JP | 2003-62467 | * | 4/2003 |
| JP | 2003-142342 A | | 5/2003 |
| JP | 2003-515573 A | | 5/2003 |
| JP | 2003-243028 A | | 8/2003 |
| JP | 2003-297677 A | | 10/2003 |
| JP | 2004-099452 A | | 4/2004 |
| JP | 2004-111294 A | | 4/2004 |
| JP | 2004-165131 A | | 6/2004 |
| JP | 2004-527902 A | | 9/2004 |
| JP | 2005-112733 A | | 4/2005 |
| JP | 2005-126382 A | | 5/2005 |
| JP | 2005-322417 A | | 11/2005 |
| WO | WO 97/02252 A1 | | 1/1997 |
| WO | WO 01/40146 A1 | | 6/2001 |
| WO | WO 02/063073 A1 | | 8/2002 |
| WO | WO 03/035609 A1 | | 5/2003 |
| WO | WO 03/106419 A1 | | 12/2003 |

OTHER PUBLICATIONS

Jin et al. "Low-Melting Dialkyl- and Bis(polyfluoroalkyl)-Substituted 1,1'-Methylenebis(imidazolium) and 1,1'-Methylenebis(1,2,4-triazolium) Bis(trifluoromethanesulfonyl)amides: Ionic Liquids Leading to Bis(N-heterocyclic carbene) Complexes of Palladium" Organometallics, 2005, vol. 24, pp. 3020-3023.*

Shu et al. "Prediction of the physical properties for the ionic liquid based on topological index." Chinese Journal of Structural Chemistry (2005), 24(9), 1083-1087.*

* cited by examiner

*Primary Examiner* — Joseph Kosack
(74) *Attorney, Agent, or Firm* — Sughrue Mion, PLLC

(57) ABSTRACT

An ionic liquid formed of a cationic component and an anionic component characterized in that the cationic component contains fluorine atoms. When defects of an oxide film formed on the surface of a metal are anodized by a two-electrode system under existence of the ionic liquid, a current-voltage curve being obtained by applying a forward voltage from 0 V at a constant voltage rate of 1 V/s has an initial peak voltage and gives a withstand voltage of 50 V or above. This ionic liquid does not evaporate easily, exhibits hydrophobicity and low hygroscopicity, and has excellent metal oxide film-repairing ability.

23 Claims, 2 Drawing Sheets though the conductivity of these liquid electrolytes is improved by adding an additive described above, it is insufficient for realizing a low impedance capacitor. In addition, in these liquid electrolytes, a dry up phenomenon is caused by evaporation of the used solvent. If the dry up occurs, both anodizability and conductivity are lost, resulting in a low heat resistance and a short life-time, which is a problem.

In order to solve these problems, a molten salt has been investigated to use as an electrolyte for a capacitor. For example, it has been investigated to constitute an electrolyte for a capacitor by, without using a solvent, melting or melting and then solidifying an electrolytic salt composed of a nitrogenous heterocyclic cation having a conjugated double bond or composed of a nitrogenous heterocyclic ring having a conjugated double bond.

Furthermore, it has been investigated to constitute a capacitor by interposing an electrolyte alone or with a separator between an anode foil and a cathode. The electrolyte for the electrolytic capacitor is in a molten state prepared by mixing carboxylate and carboxylic acid not using a solvent. However, since such an electrolyte is a solid at ambient temperature, the anodizability is significantly decreased and the conductivity property is poor. Therefore, the practical application has not been achieved yet.

On the other hand, recently, a capacitor using a solid electrolyte not containing solvents (called solid electrolytic capacitor) has been developed. Specifically, one or more electrically conductive polymers such as polypyrroles, polyanilines, polythiophenes, polyquinones, derivatives thereof, polymers prepared by polymerizing an aromatic compound containing an amino group, and polymers prepared by polymerizing an aromatic compound containing a hydroxyl group are used as an electrolyte. These conductive polymers have a significantly higher electric conductivity (electron conductivity) compared with those of liquid electrolytes using the above-mentioned known solvents. Therefore, in capacitors using these polymers as electrolytes, the internal impedance can be decreased. In particular, capacitors used in high frequency circuits show excellent characteristics. Therefore, these conductive polymer capacitors have been occupying an important position in the electrolytic capacitor market.

However, these conductive polymers do not essentially have ion conductivity and therefore are far inferior in the anodizing function for repairing an oxide film of an electrolytic capacitor to known capacitors using liquid electrolytes. It is generally thought that, in a conductive polymer capacitor, the dielectric film is prevented from breakage by insulating the conductive polymer present on the dielectric surface at the breakage portion by a dedoping reaction caused by Joule heat generated when the dielectric film is broken. This mechanism is different from that for repairing an oxide film of a capacitor using a known liquid electrolyte in the fundamental principle.

Consequently, a conductive polymer capacitor has a disadvantage that a high withstand voltage cannot be obtained. Specifically, in a conductive polymer capacitor using aluminum as an anode, the withstand voltage of the capacitor is about 16 V only by the forming at 70 V, for example, and in a conductive polymer capacitor using tantalum, the withstand voltage is about 12 V only by the forming at 34 V, for example. Here, the term "forming at 70 V" means that a direct-current voltage applied to a valve metal which becomes an anode when a dielectric oxide film is formed on the surface of the valve metal, i.e., a forming voltage (or referred to as applied voltage, the same applies hereinafter), is 70 V. Logically, it is possible to increase the withstand voltage by using a higher forming voltage. However, in such a case, the capacitor capacitance is decreased with an increase of the forming voltage, and the withstand voltage is not increased in proportion to the increase in the forming voltage. Thus, it is not a good method.

As an attempt to improve withstand voltage characteristics of such a conductive polymer capacitor, an electrolytic capacitor using an electrolyte composed of a conductive polymer and an organic acid onium salt is disclosed (for example, see Japanese Unexamined Patent Application Publication No. 2003-22938 (hereinafter referred to as Patent Document 1)). However, this organic acid onium salt is fundamentally thought to be a salt in a solid state. Therefore, in order to improve withstand voltage characteristics, the ratio of a conductive polymer (P) and an organic acid onium salt (O) is preferably (P): (O)=1:0.1 to 5, more preferably (P): (O)=1:0.2 to 2. However, in the range of this ratio, the withstand voltage characteristics are certainly improved, but the conductivity is worsened. This undesirably deteriorates the impedance characteristic of the capacitor.

Recently, remarkable molten salts which are liquids at room temperature (for example, 10 to 30° C.) have been developed independently of the technologies relating to the above-mentioned electrolytic capacitors. These are called an ionic liquid and are composed of a combination of a proper cationic component (quaternary salt cation such as imidazolium or pyridinium) and a proper anionic component ($Br^-$, $AlCl_4^-$, $BF_4^-$, or $PF_6^-$). Many ionic liquids contain a halogen. These ionic liquids are characteristically nonvolatile, nonflammable, chemically stable, and highly ion conductive and are regarded as remarkable reusable green solvents which are used in chemical reactions such as various synthesizes and catalyst reactions. However, it has not been reported that the ionic liquid is investigated from the viewpoint of anodic oxidation, namely, from the viewpoint of forming an oxide film on the surface of a valve metal or repairing an oxide film.

Further, ionic liquids are generally hydrophilic except for ones containing some anions such as $PF_6^-$ or $(CF_3SO_2)_2N^-$, and moisture may isolate a hazardous gas from an ionic liquid. For example, in 1992 Wilkes and Zaworotko disclosed [EMIm][$BF_4^-$], but it is hydrophilic and consequently has a limitation in its application field. Since these hydrophilic ionic liquids have a property to absorb moisture, an electrolytic capacitor using such a hydrophilic liquid as the electrolyte is reduced in water resistance and moisture resistance and is decreased in electric property, which is also a problem.

In addition, claim 25 of PCT Japanese Translation Patent Publication No. 2004-527902 (hereinafter referred to as Patent Document 2) discloses "A long-lived electrochemical device comprising in combination:
(a) a conjugated polymer working electrode;
(b) a counter electrode;
(c) an ionic liquid having an anion and a cation in contact with both said working electrode and said counter electrode; and
(d) a power supply for applying a voltage between said working electrode and said counter electrode, whereby a response is induced in said electrochemical device."
In Patent Document 2, the conjugated polymer (polyanion) is limited to ones electrochemically deposited on the electrodes and is characteristically an anion of an ionic liquid.
Patent Document 1: Japanese Unexamined Patent Application Publication No. 2003-22938
Patent Document 2: PCT Japanese Translation Patent Publication No. 2004-527902

DISCLOSURE OF THE INVENTION

Problems to be Solved by the Invention

It is an object of the present invention to provide an ionic liquid which has a hydrophobicity and is excellent in a function for repairing an oxide film on a metal and a method for producing the same, to provide a method for forming an oxide film on a metal surface, and to provide an electrolytic capacitor and an electrolyte.

Means for Solving the Problems

The present invention provides an ionic liquid including a cationic component and an anionic component, wherein the cationic component is characterized by containing fluorine atoms.

In the ionic liquid according to the present invention, the cationic component may contain at least one selected from the group consisting of ammonium and its derivatives, imidazolium and its derivatives, pyridinium and its derivatives, pyrrolidinium and its derivatives, pyrrolinium and its derivatives, pyradinium and its derivatives, pyrimidinium and its derivatives, triazonium and its derivatives, triazinium and its derivatives, triazine derivative cations, quinolinium and its derivatives, isoquinolinium and its derivatives, indolinium and its derivatives, quinoxalinium and its derivatives, piperazinium and its derivatives, oxazolinium and its derivatives, thiazolinium and its derivatives, morpholinium and its derivatives, and piperazine and its derivatives. In addition, the cationic component may contain a chemical structure represented by formula (1) or formula (2):

[Chemical formula 1]

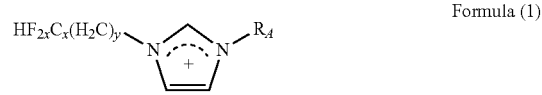

Formula (1)

(in formula (1), x denotes an integer of 1 to 20, y denotes an integer of 0 to 5, and $R_A$ denotes one selected from the group consisting of hydrogen, aliphatic hydrocarbon groups, aromatic hydrocarbon groups, carboxylic acid groups, ester groups, ether groups, acyl groups, and amino groups),

[Chemical formula 2]

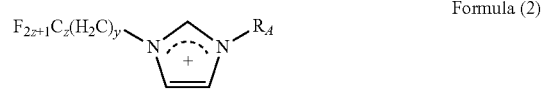

Formula (2)

(in formula (2), z denotes an integer of 1 to 20, y denotes an integer of 0 to 5, and $R_A$ denotes one selected from the group consisting of hydrogen, aliphatic hydrocarbon groups, aromatic hydrocarbon groups, carboxylic acid groups, ester groups, ether groups, acyl groups, and amino groups).

In the ionic liquid according to the present invention, the anionic component may contain fluorine atoms. In addition, the ratio of the number $n_H$ of hydrogen atoms to the number $n_F$ of fluorine atoms in the anionic component may be $n_H$:$n_F$=0:100 to 60:40. Further, the anionic component may contain a chemical structure represented by formula (3) or formula (4):

 Formula (3)

(in formula (3), x denotes an integer of 1 to 20, and y denotes an integer of 0 to 5), $$F_{2z+1}C_z(CH_2)_yOSO_3^-$$ Formula (4)

(in formula (4), z denotes an integer of 1 to 20, and y denotes an integer of 0 to 5). Further, the anionic component may contain at least one atomic group selected from the group consisting of bis(trifluoromethylsulfonyl)imide anions, $CHF_2—CF_2—CH_2OSO_3^-$ atomic groups, $CHF_2—(CF_2)_3—CH_2OSO_3^-$ atomic groups, $CF_3—(CF_2)_2—CH_2OSO_3^-$ groups, and $CF_3—(CF_2)_6—CH_2OSO_3^-$ atomic groups. In addition, the anionic component may contain an $R_B—SO_V$- atomic group (wherein v denotes an integer of 2 to 4, and $R_B$ denotes an aromatic or aliphatic compound having 1 to 50 carbon atoms). Further, the anionic component may contain a carboxyl group anion (—COO$^-$).

Furthermore, the ionic liquid according to the present invention may contain a chemical structure represented by any one of the following formulae (5) to (14).

[Chemical formula 3]

$H(F_2C)_4H_2C$—[imidazolium]—ethyl  $PF_6^-$  Formula (5)

[Chemical formula 4]

$F(F_2C)_4(H_2C)_2$—[imidazolium]—ethyl  $PF_6^-$  Formula (6)

[Chemical formula 5]

$H(F_2C)_4H_2C$—[imidazolium]—methyl  $PF_6^-$  Formula (7)

[Chemical formula 6]

$F(F_2C)_4(H_2C)_2$—[imidazolium]—methyl  $PF_6^-$  Formula (8)

[Chemical formula 7]

$C_4F_9$—[imidazolium]  $PF_6^-$  Formula (9)

[Chemical formula 8]

$F(F_2C)_4(H_2C)_2$—[imidazolium]—ethyl  $(CF_3SO_2)_2N^-$  Formula (10)

[Chemical formula 9]

$H(F_2C)_4H_2C$—[imidazolium]—$CH_3$—[phenyl]—$SO_3^-$  Formula (11)

[Chemical formula 10]

$H(F_2C)_6OCO(H_2C)_2$—[imidazolium]—ethyl  $(CF_3SO_2)_2N^-$  Formula (12)

[Chemical formula 11]

$H(F_2C)_4H_2CO_2C(H_2C)_3$—[imidazolium]—ethyl  $(CF_3SO_2)_2N^-$  Formula (13)

[Chemical formula 12]

$F(F_2C)_4(H_2C)_2$—[imidazolium]—methyl  $H(CF_2)_4CH_2OSO_3^-$  Formula (14)

Further, in the ionic liquid according to the present invention, when a defect in an oxide film formed on the surface of a metal is anodized by a two-electrode system in the presence of the ionic liquid, a current-voltage curve obtained by applying a forward voltage from 0 V at a constant voltage rate of 1 V/s can have an initial peak voltage and give a withstand voltage of 50 V or more. Here, the withstand voltage can be given to 100 V or more and the initial peak voltage can be given to 30 V or less, further to 15 V or less. In addition, the above-mentioned metal may contain at least one selected from the group consisting of aluminum and/or alloys thereof, tantalum and/or alloys thereof, and niobium and/or alloys thereof.

Further, the present invention provides a method for manufacturing the above-described ionic liquid. The method for manufacturing an ionic liquid is performed by reacting an imidazolium derivative and a fluoroalkyl halide compound.

Further, the present invention provides a method for forming an oxide film on a metal surface by anodizing the metal surface in the presence of the above-mentioned ionic liquid.

Further, the present invention provides an electrolytic capacitor provided with a function for repairing an oxide film by the above-mentioned method for forming an oxide film on a metal surface. The present invention provides an electrolytic capacitor including an electrolyte containing the above-mentioned ionic liquid and having a function for repairing oxide film.

In an electrolytic capacitor according to the present invention, the electrolyte may further contain at least one selected from the group consisting of ammonium salts, amine salts, quaternary ammonium salts, tertiary amines, and organic acids. In addition, the electrolyte may contain a conductive polymer. Here, the conductive polymer may contain at least one selected from the group consisting of polypyrroles, polyanilines, polythiophenes, polyquinones, and derivatives thereof Further, the mass ratio of the ionic liquid to the conductive polymer (ionic liquid/conductive polymer) may be 1/10000 or more and less than 1/10. In addition, the electrolyte may further contain a TCNQ salt. Here, the TCNQ salt may contain a donor composed of a nitrogenous heterocyclic compound substituted by an alkyl at the N-position and an acceptor composed of TCNQ.

Further, the present invention provides an electrolyte containing the above-mentioned ionic liquid. The electrolyte is used for forming an oxide film on a metal surface by anodic oxidation.

The electrolyte according to the present invention can be used in an electrolytic capacitor. In addition, the electrolyte according to the present invention may further contain a conductive polymer. Here, the conductive polymer may contain at least one selected from the group consisting of polypyrroles, polyanilines, polythiophenes, polyquinones, and derivatives thereof Further, the mass ratio of the ionic liquid to the conductive polymer (ionic liquid/conductive polymer) may be 1/10000 or more and less than 1/10. In addition, the electrolyte according to the present invention may further contain a TCNQ salt. Here, the TCNQ salt may contain a donor composed of a nitrogenous heterocyclic compound substituted by an alkyl at the N-position and an acceptor composed of TCNQ.

Effects of the Invention

According to the present invention, it can be provided that an ionic liquid having a hydrophobicity and being excellent in a function for repairing an oxide film on a metal and a method for producing the same, a method for forming an oxide film on a metal surface, and an electrolytic capacitor and an electrolyte.

Figure 1:
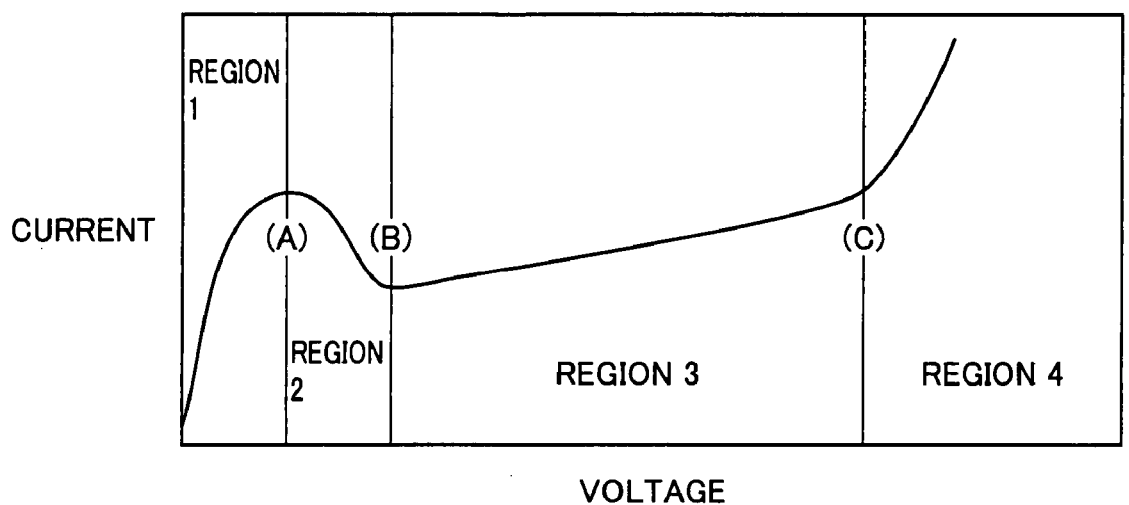
FIG. 1 shows a typical current-voltage curve which is observed in an electrolyte capable of repairing an oxide film.

DESCRIPTION OF THE REFERENCE SIGNS (A): maximum point, (B): minimum point, (C): inflection point, 10: cell, 11: cell vessel, 12: anode, 13: cathode, 14: electrolyte, 15: oxide film, 20: device for forming conductive polymer layer, 21: polymerization initiation anode, 22: etched aluminum foil, 23: dielectric layer, 24: conductive manganese layer, 25: conductive polymer layer, 26: electrolytic polymerization solution, 27: cathode for polymerization, 28: anode for polymerization

BEST MODE FOR CARRYING OUT THE INVENTION

<Ionic Liquid>

An ionic liquid according to the present invention includes a cationic component and an anionic component, and the cationic component contains fluorine atoms. The ionic liquid including a cationic component containing fluorine atoms has hydrophobicity and high ability for repairing a metal oxide film. Further, the ionic liquid according to the present invention does not vaporize readily because of the property of ionic liquids. In addition, since the ionic liquid of the present invention is hydrophobic, the hygroscopicity is low.

Here, the ionic liquid is also called room-temperature molten salt and is liquid at room temperature (for example, about 10 to 30° C.) though it is constituted of an anionic component and a cationic component. An ionic liquid is formed of ions only unlike that a usual organic solvent is partially ionized and dissociated. That is, it is thought that 100% by mass (all) of the liquid is ionized. A liquid defined as an ionic liquid is usually liquid at room temperature, but the ionic liquid used in the present invention is not necessarily required to be liquid at room temperature as long as it can become a liquid and spread to the entire electrolyte during aging treatment or heat treatment of a capacitor and become a liquid by Joule heat generated during the repair of an oxide film.

(Cationic Component of Ionic Liquid)

The cationic component of an ionic liquid according to the present invention is not specifically limited as long as the cationic component contains fluorine atoms, but preferably contains a cation having quaternary nitrogen, for example, at least one selected from the group consisting of ammonium and its derivatives, imidazolium and its derivatives, pyridinium and its derivatives, pyrrolidinium and its derivatives, pyrrolinium and its derivatives, pyradinium and its derivatives, pyrimidinium and its derivatives, triazonium and its derivatives, triazinium and its derivatives, triazine derivative cations, quinolinium and its derivatives, isoquinolinium and its derivatives, indolinium and its derivatives, quinoxalinium and its derivatives, piperazinium and its derivatives, oxazolinium and its derivatives, thiazolinium and its derivatives, morpholinium and its derivatives, and piperazine and its derivatives. In particular, among the above-mentioned cations having quaternary nitrogen, imidazolium and its derivatives, ammonium and its derivatives, and pyridinium and its derivatives are more preferable. Here, the term "derivative" means a compound obtained by substituting at least one substitutable hydrogen atom on a compound as the fundamental form with a substituent such as an aliphatic hydrocarbon group, alicyclic hydrocarbon group, aromatic hydrocarbon group, carboxyl group, ester group, ether group, acyl group, or amino group.

The cationic component of an ionic liquid according to the present invention is further preferably an imidazolium derivative containing fluorine atoms from the viewpoint that when a defect in an oxide film formed on the surface of a metal is anodized by a two-electrode system in the presence of an ionic liquid, a current-voltage curve being obtained by applying a forward voltage from 0 V at a constant voltage rate of 1 V/s has an initial peak voltage and gives a withstand voltage of 50 V or more. In particular, the cationic component most preferably contains a chemical structure represented by the following formula (1) or (2).

[Chemical formula 13]

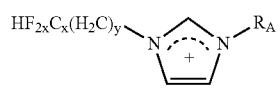

Formula (1)

[Chemical formula 14]

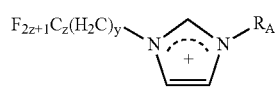

Formula (2)

Here, in formulae (1) and (2), x denotes an integer of 1 to 20, y denotes an integer of 0 to 5, z denotes an integer of 1 to 20, and $R_A$ denotes one selected from the group consisting of hydrogen, aliphatic hydrocarbon groups, aromatic hydrocarbon groups, carboxylic acid groups, ester groups, ether groups, acyl groups, and amino groups.

(Anionic Component of Ionic Liquid)

The anionic component of an ionic liquid according to the present invention preferably contains fluorine atoms from the viewpoints of increasing the hydrophobicity of the ionic liquid and of further increasing the metal oxide film-repairing ability.

From the above-mentioned viewpoints, the ratio of the number $n_H$ of hydrogen atoms to the number $n_F$ of fluorine atoms in the anionic component is preferably $n_H : n_F = 0:100$ to $60:40$. Examples of the ratio include $n_H : n_F = 0:100$, $n_H : n_F = 10:90$, $n_H : n_F = 20:80$, $n_H : n_F = 30:70$, $n_H : n_F = 40:60$, $n_H :$ $n_F$=50:50, and $n_H$: $n_F$=60:40. The ratio can be expressed by not only integers but also real numbers, but expediently expressed by rounding to the nearest whole number. Examples of the anion component having a ratio of $n_H$: $n_F$=0:100 include $BF_4^-$, $PF_6^-$, $CF_3SO_3^-$, $(CF_3SO_2)_2N^-$, and $(CF_3SO_2)_3C^-$.

In addition, from the above-mentioned viewpoints, the anionic component containing a chemical structure represented by the following formula (3) or (4) is further preferable.

  Formula (3)

  Formula (4)

Here, in formulae (3) and (4), x denotes an integer of 1 to 20, y denotes an integer of 0 to 5, and z denotes an integer of 1 to 20.

Further, from the above-mentioned viewpoints, the anionic component most preferably contains at least one atomic group selected from the group consisting of bis(trifluoromethylsulfonyl)imide anions, $CHF_2$—$CF_2$—$CH_2OSO_3^-$ atomic groups, $CHF_2$—$(CF_2)_3$—$CH_2OSO_3^-$ atomic groups, $CF_3$—$(CF_2)_2$—$CH_2OSO_3^-$ atomic groups, and $CF_3$—$(CF_2)_6$—$CH_2OSO_3^-$ atomic groups. For example, in a $CHF_2CF_2CF_2CF_2CH_2OSO_3^-$ atomic group, the ratio of $n_H$: $n_F$ is 3:8.

In addition, the anion component of an ionic liquid according to the present invention preferably contains an $R_B$—$SO_V^-$ atomic group. Here, v denotes an integer of 2 to 4, and $R_B$ denotes an aromatic or aliphatic compound having 1 to 50 carbon atoms which may have a branched structure, may contain one or more fluorine atoms, and may contain one or more substituents such as a carboxylic acid group, ester group, ether group, acyl group, or amino group.

Preferable examples of the $R_B$—$SO_V^-$-atomic group include $R_B$—$SO_3^-$ atomic groups (also referred to as sulfonate anion atomic groups, the same applies hereinafter) and $R_B$—$SO_4^-$ atomic groups (also referred to as sulfate anion atomic groups, as in $R_B$—$OSO_3^-$ atomic groups, the same applies hereinafter), and specifically p-$CH_3C_6H_4SO_3^-$, $C_6H_5SO_3^-$, $CH_3CH_2OCH_2CH_2OSO_3^-$, $C_6H_5OCH_2CH_2OSO_3^-$, $CHF_2CF_2CF_2CF_2CH_2OSO_3^-$, and $CHF_2CF_2CF_2CF_2CH_2SO_3^-$.

It is particularly preferable that the anionic component contain at least one anion selected from the group consisting of fluoroalkylsulfonate anions, fluorocycloalkylsulfonate anions, and fluorobenzylsulfonate anions. The ionic liquids containing these anionic components have high oxide film-repairing ability even if the cationic component does not contain fluorine atoms. From such a viewpoint, it is preferable that the anionic component contain at least one atomic group selected from the group consisting of $CHF_2$—$CF_2$—$CH_2SO_3^-$ atomic groups, $CHF_2$—$(CF_2)_3$—$CH_2SO_3^-$ atomic groups, $CF_3$—$(CF_2)_2$—$CH_2SO_3^-$ atomic groups, $CF_3$—$(CF_2)_6$—$CH_2SO_3^-$ atomic groups, and $CF_3$—$(CF_2)_3$—$(CH_2)_2SO_3^-$ atomic groups. In addition, from such a viewpoint, the ionic liquid further preferably contains a chemical structure represented by formula (15) or (16).

[Chemical formula 15]

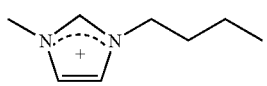  Formula (15)

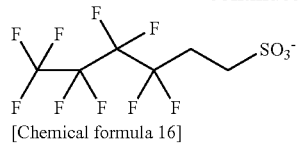

[Chemical formula 16]

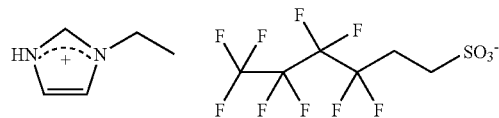  Formula (16)

In addition, the method for manufacturing an ionic liquid containing a sulfonate anion as the anionic component is not specifically limited, but a method of reacting an imidazolium derivative with an organic compound containing a sulfonate group is a preferable example.

Here, examples of fluorocycloalkylsulfonate anions include anions containing the above-mentioned fluoroalkylsulfonate anion and also a cycloalkyl group, but not limited to them. Any anions can be used as long as the anion contains a fluorocycloalkylsufonate group. Further, examples of fluorobenzylsulfonate anions include anions containing the above-mentioned fluoroalkylsulfonate anion and also a benzyl group or a fluorobenzyl group, but not limited to them. Any anion can be used as long as the anion contains a fluorobenzylsulfonate group.

In addition, the anionic component of an ionic liquid according to the present invention preferably contains a carboxyl group anion (—$COO^-$). Specifically, examples of the anionic component include $R_CCOO^-$, $^-OOCR_CCOOH$, $^-OOCR_CCCOO^-$, and $NH_2CHR_CCOO$—. Here, $R_C$ denotes a substituent such as an aliphatic hydrocarbon group, an alicyclic hydrocarbon group, an aromatic hydrocarbon group, an ether group, an ester group, or an acyl group. For example, it is effective to synthesize an ionic liquid containing a carboxyl group anion (—$COO^-$) by using formic acid, acetic acid, maleic acid, adipic acid, oxalic acid, phthalic acid, succinic acid, or an amino acid. The carboxylato suitable to the present invention is not limited to these examples.

Further, the anionic component of an ionic liquid according to the present invention preferably contains $NO_3^-$ or $R_DNO_3^-$. Here, $R_D$ denotes a substituent such as an aliphatic hydrocarbon group, an alicyclic hydrocarbon group, an aromatic hydrocarbon group, an ether group, an ester group, or an acyl group. $R_D$ may contain a fluorine atom.

Further, among ionic liquids of a twitterionic type in which a cationic component and an anionic component are covalently bonded, an ionic liquid containing a sulfonate anion ($R_B$—$SO_3^-$) or an ionic liquid containing a fluorine atom can be preferably used in the present invention.

(Hydrophobicity)

An ionic liquid is determined whether it is hydrophilic or hydrophobic by adding purified water to the ionic liquid at room temperature (25° C.) and observing if the ionic liquid and the purified water are separated into two phases or not. That is, an ionic liquid is defined to be hydrophobic when a mixture of the ionic liquid and deionized water (adding 30 ml of purified water to 30 ml of the ionic liquid in a bottle and agitating them for 5 min) is separated into two phases, a water phase and an ionic liquid phase, within 12 hr by allowing the mixture to stand at room temperature (25° C.). In addition, an ionic liquid is defined to be hydrophilic when a mixture of the ionic liquid and deionized water (adding 30 ml of purified water to 30 ml of the ionic liquid in a bottle and agitating them for 5 min) is not separated into two phases and the ionic liquid and purified water are completely mixed after the mixture has been allowed to stand at room temperature (25° C.) for 12 hr.

(Method for Manufacturing Ionic Liquid)

The ionic liquid according to the present invention is a chemical material of a combination of the above-mentioned cationic component and anionic component and can be manufactured by a known method. Specifically, an anion exchange method, an acid ester method, or a neutralization method can be used. Further, since an imidazolium derivative containing fluorine atoms is preferable as the cationic component of an ionic liquid, the ionic liquid is preferably manufactured by the reaction of an imidazolium derivative and a fluoroalkyl halide compound.

(Anodic Oxidation)

Next, anodic oxidation using an ionic liquid according to the present invention will be described. Anodic oxidation is broadly used as a means of forming an oxide film on a metal surface. An oxide film is formed on the surface of a metal by using the metal as an anode and applying a voltage or current to the anode in an electrolytic solution or in an electrolyte. This method is most commonly used as a means of forming an oxide film on the surface of, particularly, a valve metal such as aluminum, tantalum, or niobium.

(Metal)

The method for forming an oxide film according to the present invention will now be described by using aluminum as an example, but other valve metals such as tantalum and niobium are similarly used. In addition, aluminum and/or alloys thereof, tantalum and/or alloys thereof, niobium and/or alloys thereof, and other metals are the fundamentally the same. Therefore, the scope of the present invention is not limited to aluminum, and the present invention will be applied to tantalum or niobium.

(Evaluation of Anodizability of Electrolyte and Evaluation of Metal Oxide Film-Repairing Ability of Electrolyte)

The anodizability of an electrolyte is determined by measuring a change in current flowing when a cell having an anode of aluminum and a cathode of stainless steel, copper, or platinum is immersed into the electrolyte and a certain voltage is applied between the electrodes. On this occasion, the voltage applied between the anode and the cathode (referred to as applied voltage, the same applies hereinafter) is increased at a constant rate and a change in the current value is measured (this experiment is called anodizability evaluation experiment, the same applies hereinafter). That is, when the electrolyte has anodizability and an insulator of an oxide film is formed on the metal surface, the current is prevented from flowing (oxide film-forming process). However, there is a limitation in the anodizability of the electrolyte and the oxide film formed according to an increase in the applied voltage becomes not to overcome the applied voltage, and finally the oxide film is broken (oxide film breakage process). Therefore, the anodizability of an electrolyte can be estimated by measuring such a change in the current value.

The evaluation of oxide film-repairing ability of an electrolyte for an anode may be advantageously performed by using an anode having a partially induced defects by a given method, for example, previously forming an oxide film on an anode by applying a predetermined voltage in a known electrolyte and boiling the oxide film in boiling water, but is not limited to this. For example, the thus prepared sample is immersed in an electrolyte to be evaluated and a change in the current value is measured while increasing the voltage at a constant rate (this experiment is referred to as an oxide film-repairing ability evaluation experiment, the same applies hereinafter). This is also called reforming evaluation method. In this method, the same experiment as the above-mentioned anodizability evaluation experiment can be performed by, for example, selecting an applied voltage (referred to as oxide film-forming voltage, the same applies hereinafter) for previously forming an oxide film on an anode (namely, changing the thickness of an oxide film on an anode). That is, for example, the anodizability of an electrolyte can be evaluated by previously forming an oxide film at 100 V and observing the voltage when the oxide film is broken.

As mentioned above, the oxide film-repairing ability evaluation experiment can also serve as the anodizability evaluation experiment. This is also suitable for a device evaluation experiment of an electrolyte for a capacitor of the present invention. Therefore, the oxide film-repairing ability evaluation experiment is exclusively performed. FIG. 1 shows a typical change in current value (current-voltage curve) which is observed when an electrolyte has ability for repairing an oxide film.

With referring to FIG. 1, the current value first shows that the current flows through a broken portion of an oxide film (REGION 1). When the electrolyte has anodizability, a new oxide film is formed at the broken portion. Therefore, the current value increases to the maximum value (this maximum point is referred to as (A) point, the same applies hereinafter) and then decreases (REGION 2). The voltage at the (A) point is called the initial peak voltage. The minimum value (referred to as (B) point, the same applies hereinafter) of the current value is the point where the repairing of the oxide film has been completed. The voltage at the (B) point is called the repair completion voltage. Then, the current linearly increases in proportion to the voltage so as to give a current-increasing region (REGION 3). However, if the voltage is further increased, the current starts to flow apart from the linear relationship with the voltage (REGION 4) from a certain voltage (this inflexion point is referred to as (C) point, the same applies hereinafter). The voltage at the (C) point is called the withstand voltage. The withstand voltage shows the actual withstand voltage of an electrolyte and is equivalent to the voltage when the oxide film is broken. As a matter of course, when an electrolyte does not have anodizability, only the REGION 1 appears and the current value is increased, as it is doing, to break the oxide film.

As an anodic oxide film of aluminum, two types, i.e., a dense barrier-type film and a porous film, are known. A dense barrier-type film is formed in a neutral electrolyte such as borate or phosphate. A porous film is formed in an acid electrolyte such as a phosphoric acid, sulfuric acid, or oxalic acid aqueous solution. The porous film is formed because that the film is locally dissolved during the anodic oxidation. When the formation of a porous film starts by such local dissolution, protons in the electrolyte penetrate into the film by thermal action against the electric field and a large amount of ionic currents start to flow. In FIG. 1, the increase in the current value in the voltage range higher than the (C) point is caused by a sharp increase in this ionic current. It is preferable that this increase in the current occurs at a higher voltage. Therefore, the anodizability of the electrolyte can be evaluated by measuring the voltages at which the (A) point, (B) point, and (C) point appear.

That is, as an indicator of anodizability of an electrolyte, the initial peak voltage, i.e., the oxide film-forming point ((A) point), appears preferably at a lower voltage. An initial peak voltage of an electrolyte having high anodizability is more preferably 30 V or less, further preferably 15 V or less. In addition, a higher withstand voltage point ((C) point) of the electrolyte is preferable. Such a withstand voltage is more preferably 50 V or more, further preferably 100 V or more, particularly preferably 140 V or more, and most preferably 200 V or more.

Figure 2:
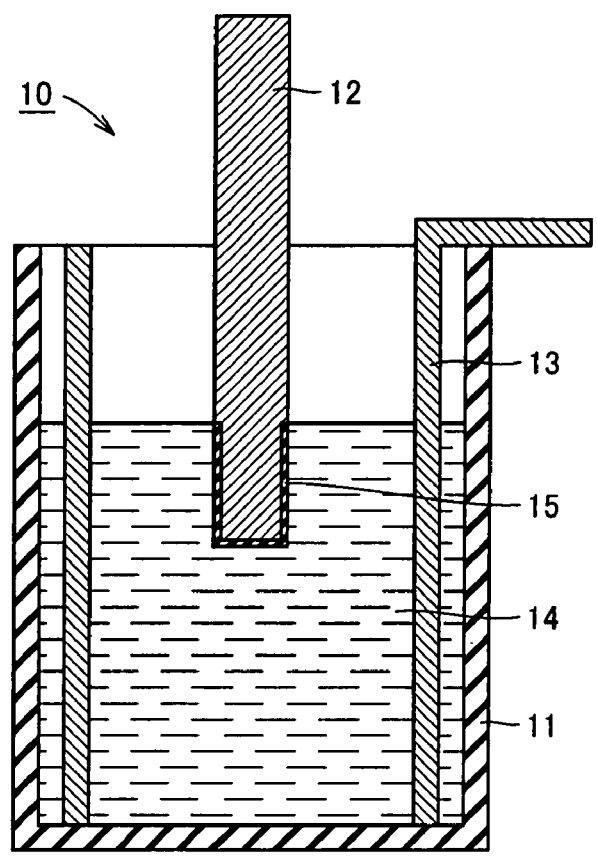
FIG. 2 is a schematic cross-sectional view of a cell used for evaluating oxide film-repairing ability and a withstand voltage.

In addition, the current-voltage curve is determined by a two-electrode system using an anode (electrode for anodic oxidation) and a cathode. However, in some cases, the evaluation can be performed by using a three-electrode system having a reference electrode for the purpose of detecting the electrode potential of either one of the anode or the cathode. FIG. 2 shows a cell used for the evaluation, but the structure of the cell is not limited to this.

Generally, as the electrolyte used for anodic oxidation, a borate chemical solution, an oxalate chemical solution, a phosphate chemical solution, or an adipate chemical solution may be used. For example, a phosphate chemical solution is prepared by dissolving 1.5 g of ammonium phosphate in 1 L (little, the same applies hereinafter) of water. An adipate chemical solution is prepared by dissolving 1 g of ammonium adipate in 1 L of water. These electrolytes are evaluated by the above-mentioned reforming method to confirm that the (A) point is in the range of 10 to 100 V, the (B) point is in 20 to 180 V, and the (C) point is in 60 to 200 V. In an acid chemical solution (electrolyte) such as an oxalate chemical solution, the (A) point appears at a lower voltage, but the (C) point also appears at a relatively low voltage. On the other hand, in a neutral solution (electrolyte) such as an adipate chemical solution, the (C) point appears at a high voltage, but the (A) point also appears at a relatively high voltage. Thus, there are disadvantages.

In an ionic liquid according to the present invention, since the cationic component contains fluorine atoms, when a defect in an oxide film formed on the surface of a metal is anodized by a two-electrode system in the presence of the ionic liquid, a current-voltage curve obtained by applying a forward voltage from 0 V at a constant voltage rate of 1 V/s can have an initial peak voltage and give a withstand voltage of 50 V or more. Here, the anodizability and oxide film-repairing ability can be enhanced by changing positions and amount of fluorine atoms to be introduced into the ionic liquid. The withstand voltage is preferably 100 V or more. In addition, the initial peak voltage is more preferably 30 V or less, further preferably 15 V or less.

Ionic liquids suitable for the present invention, namely, an ionic liquid including an anionic component containing fluorine atoms (hereinafter referred to as fluorine anion-containing ionic liquid), an ionic liquid including an anionic component containing sulfonic acid anions ($R_B$—$SO_3^-$) (hereinafter referred to as sulfonic acid anion-containing ionic liquid), and an ionic liquid including an anionic component containing carboxyl group anions (—$COO^-$) (hereinafter referred to as carboxyl group anion-containing ionic liquid), are evaluated by the above-mentioned reforming evaluation method to confirm that, for example, when the initial oxide film is formed at a voltage of 200 V, the (A) points are in the range of 10 to 25 V, the (B) points are in the range of 30 to 50 V, and the (C) points are in the range of 100 to 200 V, in almost all ionic liquids. These characteristics vary depending on the type of ionic liquid, in particular, the type of the anion. The fluorine anion-containing ionic liquid exhibits a particularly high voltage as the (C) point (for example, 160 V or more) and thus is superior in the withstand voltage characteristics. On the other hand, the (C) points of the sulfonic acid anion-containing ionic liquid and the carboxyl group anion-containing ionic liquid are about 60 to 100 V.

The differences in the (A) point, (B) point, and (C) point depending on the difference in the cationic component or anionic component of the ionic liquid described above significantly appear when the initial oxide film is formed at a voltage of 200 V or less, for example, at a voltage of 50 V or 100 V. For example, when the voltage for forming the initial oxide film is 50 V, the (C) points of the sulfonic acid anion-containing ionic liquid and the carboxyl group anion-containing ionic liquid appear at about 30 to 60 V, but the (C) point of the fluorine anion-containing ionic liquid appears at about 80 to 170 V. Further, when the voltage for forming the initial oxide film is 100 V, the (C) points of the sulfonic acid anion-containing ionic liquid and the carboxyl group anion-containing ionic liquid appear at about 50 to 80 V, but the (C) point of the fluorine anion-containing ionic liquid appears at about 120 to 200 V.

This shows that when the above-mentioned ionic liquids are used as the electrolytes, every ionic liquids exhibits excellent anodizability at a relatively low voltage region (namely, the (A) point appears at a lower voltage) compared to a case using a solvent dissolving a usual organic salt as the electrolyte. Further, it is shown that though the fluorine anion-containing ionic liquid has high withstand voltage characteristics (namely, the (C) point appears at a high voltage), electrolytes of the sulfonic acid anion-containing ionic liquid and the carboxyl group anion-containing ionic liquid have low withstand voltages (namely, the (C) points appear at a low voltage).

From the viewpoint of improving the withstand voltage characteristics of an ionic liquid, an additive, such as an ammonium salt, an amine salt, a quaternary ammonium salt, a tertiary amine, or an organic acid, is preferably added to the ionic liquid. The ionic liquid can well dissolve ammonium salts, amine salts, quaternary ammonium salts, and organic acids. Specifically, examples of the additive include ammonium salt additives such as ammonium adipate (diammonium adipate), ammonium dihydrogen phosphate, and ammonium borate; amine salt additives such as triethylamine maleate; quaternary ammonium salt additives such as quaternary ammonium maleate and quaternary ammonium phthalate; quaternary imidazolium salt additives; and organic acid additives such as malic acid and succinic acid. The addition of these additives to the above-mentioned twitterionic type ionic liquids is effective to decrease the melting points of the ionic liquids.

From the viewpoint of the purpose for enhancing ability of an ionic liquid as an electrolyte by enhancing anodizability, a solute having anodizability may be added to the ionic liquid. Since the ionic liquid does not substantially evaporate, the solute added to the ionic liquid is always present in a dissolved state. Therefore, the anodizability of the solute can enhance the anodizability of the ionic liquid and thereby the ability as an electrolyte is improved. Preferable examples of the solute include ammonium borate, ammonium phosphate, and ammonium adipate. This method is particularly effective when the anodizability of an ionic liquid is not so high. In addition, the melting point of an ionic liquid can be decreased by the freezing point-decreasing effect of the added solute as a constituent. Thus, the physical properties of an electrolyte containing an ionic liquid can be controlled.

The amount of the solute added to the ionic liquid can be optionally determined in the range in which the properties of the ionic liquid as a liquid are not lost. For example, when ammonium adipate is added to an ionic liquid, the quantity of the ammonium adipate to be added depends on the type of the ionic liquid, but, generally, is preferably 1% by mass or more and less than 50% by mass (namely, ((mass of ammonium adipate)/(mass of ionic liquid))<1) for the purpose of enhancing the anodizability. Further, when ammonium borate is added, the quantity is preferably less than 50% by mass.

Further, when ammonium phosphate is added, the quantity is preferably less than 10% by mass. The solubility of the above-mentioned solutes having anodizability in the ionic liquids is high and therefore a relatively high quantity of solute can be dissolved. This is an advantageous point in using an ionic liquid.

Further, in an ionic liquid containing $AlCl_4^-$, $Cl^-$, or $Br^-$ as the anionic component, the ionic liquid itself may dissolve an oxide film by corrosion and etching. However, when the anionic component contains fluorine atoms, the adverse effects such as etching of the oxide film do not occur. This is advantageous. Anodizability varies depending on the molecular structure. For example, an ionic liquid containing $BF_4^-$, a bis(trifluoromethylsulfonyl)imide anion (referred to as TFSI, the same applies hereinafter), a $CHF_2$—$CF_2$—$CH_2OSO_3^-$ atomic group, a $CHF_2$—$(CF_2)_3$—$CH_2OSO_3^-$ atomic group, a $CF_3$—$(CF_2)_2$—$CH_2OSO_3^-$ atomic group, or a $CF_3$—$(CF_2)_6$—$CH_2OSO_3^-$ atomic group as the anionic component containing fluorine atoms has anodizability higher than that of an ionic liquid containing $AlCl_4^-$, $Cl^-$, or $Br^-$ as the anionic component (that is, the (A) point appears at a lower voltage).

<Method for Forming Oxide Film on Metal Surface>

With reference to FIG. 2, a method for forming an oxide film on a metal surface according to the present invention is characterized by anodizing the metal surface in the presence of an ionic liquid including a cationic component containing fluorine atoms. Specifically, as shown in FIG. 2, an oxide film 15 is formed by disposing an anode 12 and a cathode 13 in a cell container 11, interposing an electrolyte 14 containing an ionic liquid including a cationic component containing fluorine atoms between the anode 12 and the cathode 13, and applying a voltage between the anode 12 and the cathode 13 to oxidize the surface of a metal as the anode 12. An ionic liquid including a cationic component containing fluorine atoms has high anodizability.

<Electrolytic Capacitor>

An electrolytic capacitor according to the present invention has a function of repairing an oxide film by the above-mentioned method for forming an oxide film on a metal surface. Even if the oxide film of such an electrolytic capacitor has a defect, the capacitor can readily repair the defect in the oxide film at a low voltage by the above-mentioned method for forming an oxide film on a metal surface. That is, the electrolytic capacitor according to the present invention contains an ionic liquid including a cationic component containing fluorine atoms as the electrolyte and has a function of repairing an oxide film. Since an electrolytic capacitor according to the present invention contains an ionic liquid including a cationic component containing fluorine atoms as the electrolyte, the capacitor has the following advantages: First, the primary advantage is that since an ionic liquid including a cationic component containing fluorine atoms has high ability for forming an oxide film and high ability for repairing an oxide film, the withstand voltage of the electrolytic capacitor is increased to elongate the life span. The secondary advantage is that since an ionic liquid including a cationic component containing fluorine atoms is hydrophobic and has a low hygroscopicity, the hygroscopicity of the electrolytic capacitor is decreased to reduce deterioration in the characteristics.

In a known electrolytic capacitor using an organic solvent such as γ-butyrolactone as the electrolyte, a solute is further added to the organic solvent and the mixture is used as a liquid electrolyte. In such an electrolyte, the organic solvent evaporates by use for a long time and the added solute is in a solid state after the evaporation of the solvent. Therefore, the solute cannot exhibit anodizability, i.e., the oxide film-repairing ability. On the other hand, in an electrolytic capacitor containing the above-mentioned ionic liquid having a low vapor pressure as the electrolyte, the above-mentioned problems are solved. Further, in a case that the organic solvent and the above-mentioned ionic liquid (used as a solute) are used as a liquid electrolyte, the solute component is allowed to be in a liquid state even if the organic solvent has evaporated. Therefore, the anodizability is not completely lost.

Therefore, the use of the ionic liquid according to the present invention in a capacitor containing a liquid electrolyte is useful as an embodiment of application of the present invention. In particular, the performance degradation of an electrolyte caused by moisture in the atmosphere can be avoided by using a hydrophobic ionic liquid among the ionic liquids, and the electrolyte can be favorably applied to a capacitor.

<Difference from Prior Literature>

Here, the difference of the present invention from prior literatures (Patent Document 1 and Patent Document 2) will be described. As described above, in Patent Document 1, as an attempt to improve withstand voltage characteristics of a conductive polymer capacitor, an electrolytic capacitor characterized by using an electrolyte composed of a conductive polymer and an organic acid onium salt is disclosed. However, it is thought that the organic acid onium salt is basically supposed to be a salt in a solid state. Therefore, for the purpose of improving the withstand voltage characteristics, the ratio of the conductive polymer (P) to the organic acid onium salt (O) is preferably (P): (O)=1:0.1 to 5, further preferably (P): (O)=1:0.2 to 2. However, in such a ratio range, the withstand voltage characteristics are certainly improved, but the conductivity characteristics are deteriorated. This degrades the impedance characteristics of the capacitor and therefore is not preferable.

Further, the long-lived electrochemical device disclosed in Patent Document 2 has not been investigated from the point of view of anodizability of an ionic liquid, namely, from the point of views of forming and repairing an oxide film. In Patent Document 2, a withstand voltage is not mentioned and also a method for forming an oxide film on a metal surface and an oxide film-repairing function of an anode are not mentioned. In addition, in Patent Document 2, an ionic liquid including a cationic component containing fluorine atoms is not mentioned at all. On the other hand, in the electrolytic capacitor according to the present invention, significant effects which are different from those of known technologies can be obtained by using an ionic liquid including a cationic component containing fluorine atoms.

(Additives)

In the electrolytic capacitor according to the present invention, the electrolyte preferably further contains at least one selected from the group consisting of ammonium salts, amine salts, quaternary ammonium salts, tertiary amines, and organic acids, in addition to the above-mentioned ionic liquid. Since these additives have high oxide film-forming ability, the oxide film-forming ability of the electrolyte can be further enhanced by adding these additives to the ionic liquid.

(Conductive Polymer)

In the electrolytic capacitor according to the present invention, the electrolyte preferably further contains a conductive polymer, in addition to the above-mentioned ionic liquid. The oxide film-forming ability of the electrolyte is enhanced by the ionic liquid and the electron conductivity of the electrolyte is enhanced by the conductive polymer.

The conductive polymer contained in the ionic liquid is not specifically limited, but the electrolyte preferably contains at least one selected from the group consisting of polypyrroles, polyanilines, polythiophenes, polyquinones, and derivatives thereof It is also preferable that the electrolyte contains at least one selected from the group consisting of polymers prepared by polymerizing an aromatic compound containing an amino group and polymers prepared by polymerizing an aromatic compound containing a hydroxyl group. Examples of these conductive polymers include a polythiophenes derived from a 3,4-dioxythiophene monomer; and a polyquinone synthesized from an aminobenzoquinone, an aminoanthraquinone, an aminonaphthoquinone, or a quinone having a hydroxyl group. The synthesis of these conductive polymers is carried out by chemical polymerization, electrolytic polymerization, or organometallic chemical condensation. In particular, chemical polymerization and electrolytic polymerization are preferable.

The electrolytic polymerization is a method for dehydrogenation polymerization by, for example, dissolving a pyrrole monomer in a solvent together with a supporting electrolyte and anodizing to deposit a conductive polymer of a polypyrrole on an anode. In general, since the oxidation-reduction potential of a polymer is lower than that of a monomer, the polymer skeleton is further oxidized during the polymerization. This allows anions of the supporting electrolyte to be introduced into the polymer as a dopant. By this mechanism, the electrolytic polymerization has an advantage that a conductive polymer can be obtained without separately adding a dopant.

On the other hand, the chemical polymerization is a synthesis method by polymerizing a monomer material such as pyrrole by dehydration oxidation in the presence of a proper oxidizing agent. Examples of the oxidizing agent include persulfate, hydrogen peroxide, and transition metal salts such as iron, copper, and manganese. In the conductive polymer synthesized by the chemical polymerization, anions of the oxidizing agent are introduced into the polymer as a dopant during the polymerization process. Therefore, a conductive polymer can be obtained by one-step reaction. When the chemical polymerization is carried out in an ionic liquid, the anionic component of the ionic liquid may be introduced into the conductive polymer as a dopant. This is particularly preferable as a method for forming an electrolyte used in the present invention.

The dopant of a conductive polymer is a constituent of the electrolyte according to the present invention and is selected in consideration of effects on the conductivity and heat stability of the conductive polymer. Preferable examples of the dopant used in the present invention include tetrafluoroborate ions ($BF_4^-$), p-toluenesulfonate ions, anthraquinone-2-sulfonate ions, triisopropylnaphthalenesulfonate ions, polyvinylsulfonate ions, dodecylbenzenesulfonate ions, alkylsulfonate ions, n-propylphosphate ions, and perchlorate ions.

In order to introduce these dopants into polymers by electrolytic polymerization, a solution is prepared by dissolving a dopant in a state of a sodium salt, ester, or ammonium salt, such as sodium p-toluenesulfonate, sodium dodecylbenzenesulfonate, n-propylphosphate ester, or ammonium tetra-n-butyl perchlorate, in a solvent such as water or a nonaqueous solvent (acetonitrile, dimethylformamide, or the like) and the above-mentioned electrolytic polymerization may be carried out in this solution.

The above-mentioned electrolyte is disposed on the surface of an oxide film formed on a valve metal, such as aluminum, tantalum, or niobium, as the electrolyte of an electrolytic capacitor. These metals function as the anode of the electrolytic capacitor and are used as an etched foil (which refers to an etched metal foil, the same applies hereinafter) or a sintered body of a metal powder, for increasing the surface area.

Therefore, the pores of the etched foil or the spaces of the sintered powder must be filled with the conductive polymer when synthesized by the chemical polymerization. On the other hand, when a conductive polymer is synthesized by the electrolytic polymerization, since the oxide film on the valve metal is a dielectric, it is necessary that a conductive film is previously formed on the dielectric for imparting conductivity to the film and then the electrolytic polymerization is carried out by applying a current or voltage from a power supply. As the conductive film, a conductive polymer synthesized by chemical polymerization or thermally decomposed manganese dioxide is preferably used.

Next, a method for compounding an ionic liquid and a conductive polymer for constituting the electrolyte according to the present invention will be described. A most simple method for compounding is one that a conductive polymer is formed on an oxide film of a valve metal by a known method and then the conductive polymer is immersed in an ionic liquid and is pulled up therefrom after some appropriate time. In addition, the ionic liquid may contain a solute having anodizability, such as ammonium borate, ammonium phosphate, or ammonium adipate. Then, when an electrolytic capacitor is formed, a cathode-forming step, an electrode-mounting step, an armoring step, and an aging step may be sequentially performed. Further, if an aluminum case is used as in a toroidal electrolytic capacitor, the ionic liquid is preferably put in the aluminum case.

The amount of the ionic liquid added to the electrolyte is determined in the range that satisfactory anodizability can be obtained and the electron conductivity of the conductive polymer is not impaired. Generally, from the viewpoint of not impairing the electron conductivity, the mass ratio of the added ionic liquid to the conductive polymer is preferably less than 1/10. On the other hand, from the viewpoint of obtaining satisfactory anodizability, the mass ratio of the added ionic liquid to the conductive polymer is preferably not less than 1/10000, more preferably not less than 1/1000. That is, the mass ratio of the ionic liquid to the conductive polymer (ionic liquid/conductive polymer) is preferably in the range of 1/10000 or more and less than 1/10, more preferably in the range of 1/1000 or more and less than 1/10.

The amount of an ionic liquid added to the electrolyte of an electrolytic capacitor according to the present invention may be significantly small compared to that required to an organic acid onium salt of an electrolytic capacitor using an electrolyte consisting of a conductive polymer and the organic acid onium salt disclosed in Patent Document 1. In Patent Document 1, for the purpose of improving the withstand voltage characteristics, the preferable ratio of the conductive polymer (P) to the organic acid onium salt (O) is (P): (O)=1:0.1 to 5, more preferably (P): (O)=1:0.2 to 2. However, in the electrolyte according to the present invention, the preferable mass ratio of the ionic liquid to the conductive polymer is less than 1/10. By the addition of such a small amount of the ionic liquid, the high electric conductivity characteristics of the conductive polymer are maintained. Thus, a capacitor having excellent impedance characteristics can be realized.

In a second method for compounding, an ionic liquid is used as an solvent for synthesizing a conductive polymer by electrolytic polymerization or chemical polymerization, and the ionic liquid is allowed to willingly remain in the steps after, for example, a step for forming the electrolyte of an electrolytic capacitor. The mass ratio of the ionic liquid to the conductive polymer (ionic liquid/conductive polymer) in this case is also preferably in the range of 1/10000 or more and less than 1/10, more preferably in the range of 1/1000 or more and less than 1/10.

Further, it is more preferable for compounding in this case that the type of anion of the ionic liquid is common to the anion of the dopant of the conductive polymer. By using the common anion, the doping to the conductive polymer can be conducted simultaneous with the electrolytic polymerization and thereby an electrolyte having excellent electron conductivity and excellent ionic conductivity can be obtained. These methods, i.e., an ionic liquid is used as a solvent in the synthesis of a conductive polymer by chemical polymerization, the ionic liquid after the polymerization is allowed to willingly remain, and an ionic liquid is added to the polymerized conductive polymer, are not conventionally known.

(TCNQ Salt)

The electrolyte according to the present invention preferably contain a TCNQ (which refers to tetracyanoquinodimethane, the same applies hereinafter) salt. The TCNQ salt is not specifically limited, but a TCNQ complex salt using an ammonium cation is preferably used. In particular, a TCNQ complex salt containing a donor composed of a nitrogenous heterocyclic compound substituted by an alkyl at the N-position and an acceptor composed of TCNQ is further preferably used. Examples of the nitrogenous heterocyclic compound include pyridine and its derivatives such as lutidine; quinoline and its derivatives such as isoquinoline; acridine; phenazine; and phenanthroline. Examples of the alkyl group at the N-position include butyl, amyl, hexyl, and phenethyl. As the electrolyte, these TCNQ salts are used alone or as a mixture of two or more, and an additive such as a glucose polymer may be added according to need. The TCNQ salt is synthesized by dissolving TCNQ in a solvent such as purified and dehydrated acetonitrile, adding an ammonium salt (for example, N-n-butylisoquinolinium iodide) thereto, and filtering and collecting the precipitated TCNQ salt.

Examples of the TCNQ salt include N-n-butylisoquinolinium $(TCNQ)_2$ salt, N-isoamylisoquinolinium $(TCNQ)_2$ salt, N,N-pentamethylene (lutidine)$_2$ $(TCNQ)_4$ salt, N-phenethyl-lutidine $(TCNQ)_2$ salt, and mixtures of these TCNQ salts. The reasons why these TCNQ salts are particularly preferably used are that these salts have relatively high conductivity and have the peculiar property, as a TCNQ salt, of being molten by heating. General TCNQ salts are decomposed or sublimed by heating, not molten by heating. The electrolyte of an electrolytic capacitor is disposed on the surface of a dielectric oxide film formed on a valve metal, such as aluminum, tantalum, or niobium. These metals function as the anode of an electrolytic capacitor and are used as an etched foil or a sintered body of a metal powder, for increasing the surface area. Therefore, the pores of the etched foil or the spaces of the sintered powder must be filled with the TCNQ salt. The TCNQ salt property of being molten is used for filling the inside of an etched aluminum electrode or a sintered tantalum electrode with the TCNQ salt and is useful in a manufacturing method.

The amount of the ionic liquid added to the electrolyte is determined in the range that satisfactory anodizability can be obtained and the electron conductivity of the TCNQ salt is not impaired. Generally, from the viewpoint of not impairing the electron conductivity, the mass ratio of the ionic liquid to the TCNQ salt (ionic liquid/TCNQ salt) is preferably less than 1/2, more preferably 1/5 or less, further preferably 1/10 or less. On the other hand, from the viewpoint of obtaining satisfactory anodizability, the mass ratio of the ionic liquid to the TCNQ salt (ionic liquid/TCNQ salt) is preferably not less than 1/10000, more preferably not less than 1/1000. That is, the mass ratio of the ionic liquid to the TCNQ salt (ionic liquid/TCNQ salt) is preferably in the range of 1/10000 or more and less than 1/2, more preferably in the range of 1/10000 or more and 1/5 or less, further preferably 1/1000 or more and 1/10 or less.

Next, a method for compounding the ionic liquid and the TCNQ salt for constituting the electrolyte according to the present invention will be described. This method for compounding is capable of obtaining an electrolyte having excellent electron conductivity and the excellent anodizability.

A most simple method for compounding is one that a TCNQ salt is formed on an oxide film of a valve metal by a known method and then the TCNQ salt is immersed in an ionic liquid and is pulled up therefrom. Then, when an electrolytic capacitor is formed, a cathode-forming step, an electrode-mounting step, an armoring step, and an aging step may be sequentially performed.

In a toroidal capacitor using an aluminum case, an ionic liquid and a TCNQ salt are added into the aluminum case and are heated to be molten. Then, a capacitor element coiled together with Manila hemp paper and including an anode and a cathode is inserted in the aluminum case and impregnated with the ionic liquid and the TCNQ salt. When an electrolytic capacitor is formed, a sealing step and an aging step may be sequentially performed. For a capacitor which is not a toroidal type, the TCNQ salt may be formed on an oxide film of a valve metal by a known method, immersed in the ionic liquid, and then pulled up therefrom. When an electrolytic capacitor is formed, a cathode mounting step, an armoring step, and an aging step may be sequentially performed.

(Configuration of Electrolytic Capacitor)

Next, a specific configuration of an electrolytic capacitor which uses an ionic liquid including a cationic component containing fluorine atoms (hereinafter referred to as fluorine cation-containing ionic liquid) as the electrolyte and a method for manufacturing the same will be described.

1. Aluminum/Oxide Film/(Polypyrrole+Fluorine Cation-Containing Ionic Liquid) System Electrolytic Capacitor This electrolytic capacitor can be obtained by forming a conductive polymer on an oxide film of aluminum by electrolytic polymerization and then adding a fluorine cation-containing ionic liquid thereto.

That is, a 7 mm by 10 mm etched aluminum foil formed with fine pores on the surface by etching (referring to an aluminum foil received etching treatment, the same applies hereinafter) and provided with an anode lead is immersed in a 3% by mass ammonium adipate aqueous solution, and anodic oxidation is carried out by applying a voltage of 70 V at 70° C. to form an oxide film as a dielectric film on the surface of the etched aluminum foil. Then, the aluminum foil is immersed in a 30% by mass manganese nitrate aqueous solution, then air-dried, and subjected to heat decomposition treatment at 300° C. for 30 min to form a conductive layer composed of a manganese oxide layer on the dielectric film.

Figure 3:
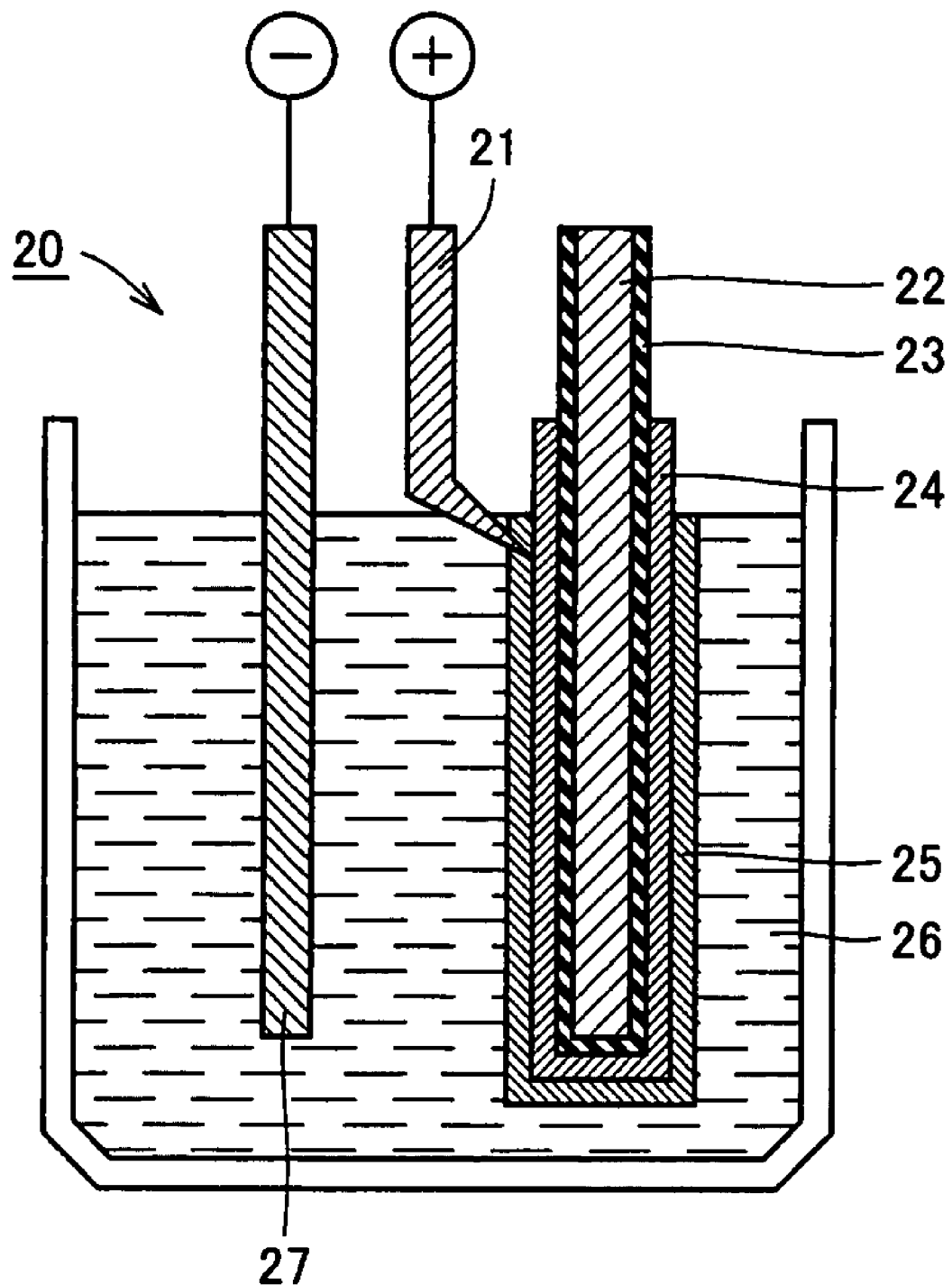
FIG. 3 is a schematic cross-sectional view of a device for forming a conductive polymer layer.

Then, a conductive polymer layer of a polypyrrole layer is formed on the etched aluminum foil by electrolytic polymerization. FIG. 3 is a schematic view of a conductive polymer layer-forming device 20. With reference to FIG. 3, an electrolytic polymerization solution 26 used for polymerization is a methanol (30% by mass)-water mixture solution containing 0.5 M ("M" means molar concentration (mol/L), the same applies hereinafter) pyrrole and 0.1 M sodium triisopropylnaphthalenesulfonate. A polymerization anode prepared by sequentially forming a dielectric layer 23 and a manganese dioxide conductive layer 24 on an etched aluminum foil 22 is disposed in the electrolytic polymerization solution 26. A polymerization initiation anode 21 is brought in the vicinity of the manganese dioxide conductive layer 24, and a constant voltage of 1.5 V is applied between the polymerization initiation anode 21 and a polymerization cathode 27 for 50 min to conduct an electrolytic polymerization reaction. Thus, a conductive polymer layer 25 of an electrolytically polymerized polypyrrole layer is formed on the manganese dioxide conductive layer 24.

The conductive layer is washed with water and dried, and is then immersed in a methanol solution of the fluorine cation-containing ionic liquid. Then, the fluorine cation-containing ionic liquid is added to the electrolytically polymerized polypyrrole layer (conductive polymer layer 25) by removing methanol by drying. Thus, an electrolyte according to the present invention is obtained. The amount of the fluorine cation-containing ionic liquid is controlled so as to be 0.5 to 5% by mass of the conductive polymer. Then, a carbon layer and a silver paste layer are sequentially formed on the above-mentioned electrolyte. The silver paste layer is provided with a cathode lead, and aging is performed at an applied voltage of 12.5 V for 1 hr. After armoring with a resin, an electrolytic capacitor of the present invention is obtained. Though the initial capacitance, tan δ, and impedance (120 Hz) values of this electrolytic capacitor are not largely different from those of an electrolytic capacitor to which the fluorine cation-containing ionic liquid is not added, the withstand voltage value is increased. In addition, the capacitor characteristic values of the electrolytic capacitor to which the fluorine cation-containing ionic liquid is added are measured after the aging at 20 V for 1 hr. Further, the withstand voltage is measured as a voltage when a leakage current starts to increase when a voltage is raised at a constant rate. In the measurement of withstand voltage, the measurement error is large. Therefore, an average value of measurements of ten electrolytic capacitor elements is used. The same applies electrolytic capacitors below.

2. Aluminum/Oxide Film/(Methoxyphenol-Containing Polypyrrole+Fluorine Cation-Containing Ionic Liquid) System Electrolytic Capacitor This electrolytic capacitor is produced as in the above 1 except that a methanol (30% by mass)-water mixture solution containing 0.15 M methoxyphenol, 0.5 M pyrrole (0.5 M), and 0.1 M sodium triisopropylnaphthalenesulfonate is used as an electrolytic polymerization solution for forming a conductive polymer layer by electrolytic polymerization.

Though the initial capacitance, tan δ, and impedance values of this electrolytic capacitor are not largely different from those of an electrolytic capacitor to which the fluorine cation-containing ionic liquid is not added, the withstand voltage value is increased.

3. Tantalum/Oxide Film/(Polypyrrole+Fluorine Cation-Containing Ionic Liquid) System Electrolytic Capacitor This electrolytic capacitor can be obtained by forming a conductive polymer on an oxide film of tantalum by chemical polymerization and then adding a fluorine cation-containing ionic liquid thereto.

That is, an element is formed by anodizing a rectangular parallelepiped tantalum sintered body (2 mm in length, 1.5 mm in height, and 1 mm in width) provided with an anode lead in a 0.05% by mass phosphoric acid aqueous solution under conditions at an applied voltage of 33.9 V at 85° C. for 60 min to form an oxide film as a dielectric film on the tantalum sintered body. This element is immersed in a 0.75 M pyrrole aqueous solution for 2 min and then immersed in a 0.1 M ferric sulfate aqueous solution for 10 minutes. This operation is repeated about 20 times to form a polypyrrole layer as a conductive layer on the oxide film. Then, the element provided with the polypyrrole layer is washed with water, dried, then immersed in a methanol solution of a fluorine cation-containing ionic liquid, and then dried to remove the methanol. By the above-described method, the fluorine cation-containing ionic liquid is added to the chemically polymerized polypyrrole layer to obtain an electrolyte of the present invention. The amount of the fluorine cation-containing ionic liquid is controlled to 0.5 to 5% by mass of the conductive polymer. Then, a carbon layer and a silver paste layer are sequentially formed on the electrolyte. The silver paste layer is provided with a cathode lead, and aging is performed at an applied voltage of 12.5 V for 1 hr. After armoring with a resin, an electrolytic capacitor of the present invention is obtained. Though the initial capacitance and tan δ values of this electrolytic capacitor are not largely different from those of an electrolytic capacitor to which the fluorine cation-containing ionic liquid is not added, the leakage current value is decreased and the withstand voltage value is increased.

4. Aluminum/Oxide Film/(Polythiophene+Fluorine Cation-Containing Ionic Liquid) System Electrolytic Capacitor This electrolytic capacitor can be obtained by forming a polythiophene layer as a conductive polymer on an oxide film of aluminum by chemical polymerization and then adding a fluorine cation-containing ionic liquid thereto.

That is, a 4 mm by 3.3 mm etched aluminum foil is immersed in a 3% by mass ammonium adipate aqueous solution. Then, the applied voltage is increased from 0 V to 10 V at a rate of 10 mV/sec, and a constant voltage of 10 V is applied for 40 min to form a dielectric film on the surface of the etched aluminum foil. Then, the etched aluminum foil provided with the dielectric film is washed with flowing deionized water for 10 min and then dried at 105° C. for 5 min. The capacitance of the thus obtained etched aluminum foil in a solution is measured. Here, the capacitance of an etched aluminum foil in a solution means an electrostatic capacity of an electrode and is calculated from an inclination of a v-t (voltage-time) curve in a constant current charge/discharge test in a solution.

Then, an ethanol solution containing ferric benzenesulfonate and ferric triisopropylnaphthalenesulfonate is prepared as an oxidizing agent solution. Ferric benzenesulfonate is a transition metal salt including a benzenesulfonate ion as an anion, and ferric triisopropylnaphthalenesulfonate is a transition metal salt including a triisopropylnaphthalenesulfonate ion as an anion. Then, 3,4-dioxythiophene is mixed with the oxidizing agent solution, and the resulting mixture is stirred to prepare a polymerization solution. The etched aluminum foil provided with a dielectric film (oxide film) is immersed in this polymerization solution and heated in an electric furnace at 105° C. for 5 sec, further heated in an electric furnace at 70° C. for 10 min to progress chemical polymerization, and washed with deionized water, and then dried. This operation is repeated ten or more times so that the entire foil is covered with polythiophene on visual inspection. After washing and drying, a fluorine cation-containing ionic liquid is added to the polythiophene layer by the same method as in the above 1. (That is, as described above, a polythiophene layer is formed on a conductive layer by electrolytic polymerization and the layer is washed with water, dried, immersed in a methanol solution of a fluorine cation-containing ionic liquid, and then dried to remove methanol. By this method, the fluorine cation-containing ionic liquid is added to the electrolytically polymerized polythiophene layer to obtain an electrolyte of the present invention. The amount of the fluorine cation-containing ionic liquid is controlled to 0.5 to 5% by mass of the conductive polymer.) Then, a carbon layer and a silver paste layer are sequentially formed on the electrolyte of the present invention. The silver paste layer is provided with a cathode lead, and aging is performed at an applied voltage of 12.5 V for 1 hr. After armoring with a resin, an electrolytic capacitor of the present invention is obtained. Though the initial capacitance and tan δ values of this electrolytic capacitor are not largely different from those of an electrolytic capacitor to which the fluorine cation-containing ionic liquid is not added, the leakage current value is decreased and the withstand voltage value is increased.

5. Aluminum/Oxide Film/(Polypyrrole+Fluorine Cation-Containing Ionic Liquid+Solute) System Electrolytic Capacitor This electrolytic capacitor is produced as in the above 1 except that the methanol solution of a fluorine cation-containing ionic liquid further contains a solute having oxide film (dielectric film)-forming ability at a mass ratio of the solute to the ionic liquid being 1/2. That is, the step of immersion in a methanol solution of an ionic liquid in the above 1 is carried out using the above-mentioned methanol solution of the ionic liquid containing a solute.

Here, as the above-mentioned solute, ammonium adipate (diammonium adipate=$(NH_4)^+(^-OOC-(CH_2)_4-COO^-)$ $(NH_4)^+$, abbreviated as SA hereinafter), triethylamine maleate (triethylammonium hydrogen maleate=$((C_2H_5)_3N-H)^+$ $(HOOC-CH=CH-COO)^-$, abbreviated as SB hereinafter), tetraethylammonium maleate (triethylammonium hydrogen maleate=$((C_2H_5)_4N)^+(HOOC-CH=CH-COO)^-$, abbreviated as SC hereinafter), tetraethylammonium phthalate $(((C_2H_5)_4N)^+(HOOC-C_6H_4-COO)^-$, abbreviated as SD hereinafter), tetraethylammonium benzoate $(((C_2H_5)_4N)^+(C_6H_5-COO)^-$, abbreviated as SE hereinafter), triethylmethylammonium maleate (triethylmethylammonium hydrogen maleate=$((C_2H_5)_3N-CH_3)^+(HOOC-CH=CH-COO)^-$, abbreviated as SF hereinafter), triethylmethylammonium phthalate (triethylmethylammonium hydrogen phthalate=$((C_2H_5)_3N-CH_3)^+(1-HOOC-C_6H_4-2-COO)^-$, abbreviated as SG hereinafter), or phosphoric acid ($H_3PO_4$, abbreviated as SH hereinafter) is used. By forming an electrolytic capacitor by using an electrolyte of which conductive polymer is impregnated with the ionic liquid containing the above-mentioned solute according to the present invention, the electrolytic capacitor can give a further high withstand voltage.

6. Aluminum/Oxide Film/(Polypyrrole+Fluorine Cation-Containing Ionic Liquid+Solute) System Electrolytic Capacitor This electrolytic capacitor is produced as in the above 1 except that (1) at the time of forming the conductive polymer layer by electrolytic polymerization, the conductive polymer is formed by electrolytic polymerization using a methanol (30% by mass)-water mixture solution containing 0.15 M methoxyphenol, 0.5 M pyrrole, and 0.1 M sodium triisopropylnaphthalenesulfonate and (2) at the time of adding the fluorine cation-containing ionic liquid, the fluorine cation-containing ionic liquid containing solute SA at a mass ratio of the solute to the ionic liquid being 15/85 is used. Though the initial capacitance, tan δ, and impedance values of this electrolytic capacitor are not largely different from those of an electrolytic capacitor to which the fluorine cation-containing ionic liquid is not added, the withstand voltage value is increased.

7. Aluminum/Oxide Film/(Polypyrrole+Fluorine Cation-Containing Ionic Liquid+Solute) System Electrolytic Capacitor This electrolytic capacitor is produced as in the above 6 except that the fluorine cation-containing ionic liquid containing solute SB, SF, or SG at a mass ratio of the solute to the ionic liquid being 15/85 is used in the above 6 (2). Though the initial capacitance, tan δ, and impedance values of this electrolytic capacitor are not largely different from those of an electrolytic capacitor to which the fluorine cation-containing ionic liquid is not added, the withstand voltage value is increased. In other words, any types of solutes added to the ionic liquid can enhance the withstand voltage as long as the solute has oxide film-forming ability.

8. Initial Characteristics of Capacitor: Tantalum/Oxide Film/(Polypyrrole+Fluorine Cation-Containing Ionic Liquid+Solute) System Electrolytic Capacitor This electrolytic capacitor can be produced by forming a conductive polymer on an oxide film of tantalum by chemical polymerization and then adding a fluorine cation-containing ionic liquid containing solute SA thereto. The mass ratio of the solute to the ionic liquid is 15/85.

That is, a dielectric film is formed by anodizing a rectangular parallelepiped tantalum sintered body (2 mm in length, 1.5 mm in height, and 1 mm in width) provided with an anode lead in a 0.05% by mass phosphoric acid aqueous solution under conditions at an applied voltage of 33.9 V at 85° C. for 60 min. This element is immersed in a 0.75 M pyrrole aqueous solution for 2 min and then immersed in a 0.1 M ferric sulfate aqueous solution for 10 min. This operation is repeated about 20 times to form a polypyrrole layer as a conductive polymer layer on the dielectric film. Then, an ionic liquid is added thereto by the same method as that in the above 2. Then, a carbon paste layer and a silver paste layer are formed by a usual method. The silver paste layer is provided with a cathode lead, and aging is performed at an applied voltage of 12.5 V. After armoring with a resin, an electrolytic capacitor of the present invention is obtained. Though the initial capacitance and tan δ values of this electrolytic capacitor are not largely different from those of an electrolytic capacitor to which the fluorine cation-containing ionic liquid is not added, the leakage current value is decreased and the withstand voltage value is increased.

9. Aluminum/Oxide Film/(Polythiophene+Fluorine Cation-Containing Ionic Liquid+Solute) System Electrolytic Capacitor This electrolytic capacitor is produced by forming polythiophene as a conductive polymer on an oxide film of aluminum by chemical polymerization and then adding a fluorine cation-containing ionic liquid containing solute SA thereto. The mass ratio of the solute to the ionic liquid is 15/85.

That is, a 4 mm by 3.3 mm etched aluminum foil is immersed in a 3% by mass ammonium adipate aqueous solution. Then, the applied voltage is increased from 0 V to 10 V at a rate of 10 mV/sec, and a constant voltage of 10 V is applied for 40 min to form a dielectric film. Then, the foil is washed with flowing deionized water for 10 min and then dried at 105° C. for 5 min. The capacitance of the thus obtained etched aluminum foil in a solution is measured.

Then, an ethanol solution containing ferric benzenesulfonate and ferric triisopropylnaphthalenesulfonate is prepared as an oxidizing agent solution. Ferric benzenesulfonate is a transition metal salt including a benzenesulfonate ion as an anion, and ferric triisopropylnaphthalenesulfonate is a transition metal salt including a triisopropylnaphthalenesulfonate ion as an anion. Then, 3,4-dioxythiophene is mixed with the oxidizing agent solution, and the resulting mixture is stirred to prepare a polymerization solution. The above-mentioned anodized aluminum foil is immersed in this polymerization solution and heated in an electric furnace at 105° C. for 5 sec, further heated in an electric furnace at 70° C. for 10 min to progress chemical polymerization, and washed with deionized water, and then dried. This operation is repeated so that the entire etched aluminum foil is covered with polythiophene. After washing and drying, the above-mentioned fluorine cation-containing ionic liquid containing solute SA is added thereto by the same method as in the above 1. Then, a cathode is formed with a carbon paste and silver paint. The cathode (silver paste layer) is provided with a cathode lead, and aging is performed at an applied voltage of 12.5 V for 1 hr. After armoring with a resin, an electrolytic capacitor of the present invention is obtained. Though the initial capacitance and tan δ values of this electrolytic capacitor are not largely different from those of an electrolytic capacitor to which the fluorine cation-containing ionic liquid is not added, the leakage current value is decreased and the withstand voltage value is increased.

10. Aluminum/Oxide Film/(N-n-butylisoquinolinium $(TCNQ)_2$ Salt+Fluorine Cation-Containing Ionic Liquid) System Electrolytic Capacitor This electrolytic capacitor is produced by synthesizing a TCNQ salt on an oxide film of aluminum by melting and impregnating and then adding a fluorine cation-containing ionic liquid thereto.

That is, an etched aluminum foil formed with fine pores is immersed in a 3% by mass ammonium adipate aqueous solution, and anodic oxidation is carried out under conditions at an applied voltage of 50 V at 70° C. for forming an oxide film as a dielectric film on the surface of the etched aluminum foil. Then, this is used as an anode foil/cathode foil, and lead wires are attached thereto. Then, the foil is coiled through a separator of Manila hemp paper to form a toroidal capacitor element. Then, in order to facilitate impregnation of the molten TCNQ salt, this capacitor element is heated to carbonize the separator.

Then, an armoring aluminum case is filled with an N-n-butylisoquinolinium $(TCNQ)_2$ salt and a fluorine cation-containing ionic liquid (the mass ratio (N-n-butylisoquinolinium $(TCNQ)_2$ salt): (fluorine cation-containing ionic liquid)=98:2) as an electrolyte, followed by melting at 210° C. Then, the above-mentioned capacitor element is pre-heated and is placed in this aluminum case, and the aluminum case is cooled with liquid nitrogen immediately after the element is placed in the case. Then, an epoxy resin is injected into an upper portion of the case and then heat-cured to seal the case. Thus, an electrolytic capacitor of the present invention is obtained.

Though the initial capacitance, tan δ, and impedance values of this electrolytic capacitor are not largely different from those of an electrolytic capacitor to which the fluorine cation-containing ionic liquid is not added, the withstand voltage value is increased. In other words, the withstand voltage is increased by adding a TCNQ salt to the electrolyte.

11. Aluminum/Oxide Film/(N-n-butylisoquinolinium $(TCNQ)_2$ Salt+Fluorine Cation-Containing Ionic Liquid) System Electrolytic Capacitor This electrolytic capacitor is produced as in the above 10 by forming a TCNQ salt electrolyte by melting and impregnating and then adding a fluorine cation-containing ionic liquid thereto. Though the initial capacitance, tan δ, and impedance values of the thus obtained electrolytic capacitor are not largely different from those of an electrolytic capacitor to which the fluorine cation-containing ionic liquid is not added, the withstand voltage value is increased.

12. Aluminum/Oxide Film/(N-isoamylisoquinolinium $(TCNQ)_2$ Salt+Fluorine Cation-Containing Ionic Liquid) System Electrolytic Capacitor This electrolytic capacitor can be produced by the same method as that in the above 10 except that an N-isoamylisoquinolinium $(TCNQ)_2$ salt is used instead of the N-n-butylisoquinolinium $(TCNQ)_2$ salt. In addition, the melting temperature is 215° C. Though the initial capacitance, tan δ, and impedance values of this electrolytic capacitor are not largely different from those of an electrolytic capacitor to which the fluorine cation-containing ionic liquid is not added, the withstand voltage value is increased. In other words, the withstand voltage of an electrolytic capacitor is increased, even if a different TCNQ salt is used, by using an electrolyte to which a fluorine cation-containing ionic liquid is added according to the present invention.

13. Aluminum/Oxide Film/(N-n-isoamylisoquinolinium-butylisoquinolinium $(TCNQ)_2$ Salt+Fluorine Cation-Containing Ionic Liquid) System Electrolytic Capacitor This electrolytic capacitor is produced by the same method as that in the above 10 except that an N-n-isoamylisoquinoliniumbutylisoquinolinium $(TCNQ)_2$ salt is used instead of an N-n-butylisoquinolinium $(TCNQ)_2$ salt. In addition, the melting temperature is 215° C. Though the initial capacitance, tan δ, and impedance values of this electrolytic capacitor are not largely different from those of an electrolytic capacitor to which the fluorine cation-containing ionic liquid is not added, the withstand voltage value is increased.

14. Aluminum/Oxide Film/(N-n-butylisoquinolinium $(TCNQ)_2$ Salt+Fluorine Cation-Containing Ionic Liquid+Solute) System Electrolytic Capacitor This electrolytic capacitor is produced as in the above 10 except that any one of the above-mentioned solutes SA, SB, SC, SD, and SE is added to an ionic liquid so that the mass ratio of the ionic liquid to the solute is 80:20. The withstand voltage of an electrolytic capacitor is further increased by using an electrolyte prepared by adding a fluorine cation-containing ionic liquid containing the above-mentioned solute to the TCNQ salt.

15. Aluminum/Oxide Film/(N-n-butylisoquinolinium $(TCNQ)_2$ Salt+Fluorine Cation-Containing Ionic Liquid+Solute) System Electrolytic Capacitor This electrolytic capacitor is produced as in the above 10 except that solute SA is added to a fluorine cation-containing ionic liquid so that the mass ratio of the ionic liquid to the solute is 85:15 and this ionic liquid is added to a TCNQ salt so that the mass ratio of the ionic liquid to the TCNQ salt is 5:95 and the resulting mixture is used as an electrolyte.

Though the initial capacitance, tan δ, and impedance values of this electrolytic capacitor are not largely different from those of an electrolytic capacitor to which the fluorine cation-containing ionic liquid is not added, the withstand voltage value is increased.

16. Aluminum/Oxide Film/(N-n-butylisoquinolinium $(TCNQ)_2$ Salt+Fluorine Cation-Containing Ionic Liquid+Solute) System Electrolytic Capacitor This electrolytic capacitor is produced as in the above 15 except that any one of solutes SB, SC, SD, and SE is used instead of solute SA.

Though the initial capacitance, tan δ, and impedance values of this electrolytic capacitor are not largely different from those of an electrolytic capacitor to which the fluorine cation-containing ionic liquid is not added, the withstand voltage value is increased.

17. Aluminum/Oxide Film/(Polypyrrole+Fluorine Cation-Containing Liquid) System Electrolytic Capacitor This electrolytic capacitor is produced by the same method as that in the above 1 except that the amount of a fluorine cation-containing liquid is varied in the range of 0.01 to 10 parts by mass to 100 parts by mass of polypyrrole as a conductive polymer.

The withstand voltage-increasing effect is recognized even if the amount of the fluorine cation-containing ionic liquid added to a conductive polymer (polypyrrole) is only 0.01 parts by weight to 100 parts by weight of the conductive polymer. When the amount is 0.1 parts by weight or more, the effect is significant. However, when the amount to be added is 10 parts by weight or more, the impedance characteristics are deteriorated and the initial capacitance also tends to be decreased.

The similar tendency is observed in any cases that tantalum is used as an electrode; a conductive polymer other than pyrrole, such as thiophene, is used; and the polymerization is conducted electrolytically or chemically. On the bases of these results, in an electrolyte including a conductive polymer and a fluorine cation-containing ionic liquid, the preferable amount of the ionic liquid is 0.01 parts by mass or more and less than 10 parts by mass to 100 parts by mass of the conductive polymer, namely, the mass ratio of the ionic liquid to the conductive polymer (ionic liquid/conductive polymer) is preferably 1/1000 or more and less than 1/10.

18. Aluminum/Oxide Film/(N-n-butylisoquinolinium (TCNQ)$_2$ Salt+Fluorine Cation-Containing Ionic Liquid) System Electrolytic Capacitor This electrolytic capacitor is produced by the same method as that in the above 10 except that the amount of the fluorine cation-containing ionic liquid to 100 parts by mass of the TCNQ salt is varied in the range of 0.01 to 10 parts by weight.

The withstand voltage-increasing effect is recognized even if the amount of the fluorine cation-containing ionic liquid added to a TCNQ salt is only 0.01 parts by weight to 100 parts by weight of the TCNQ salt. When the amount is 0.1 parts by weight or more, the effect is significant. However, when the amount to be added is 10 parts by weight or more, the impedance characteristics are deteriorated and the initial capacitance also tends to be decreased. On the bases of these results, in an electrolyte including a TCNQ salt and a fluorine cation-containing ionic liquid, the preferable amount of the ionic liquid is 0.01 parts by mass or more and less than 10 parts by mass to 100 parts by mass of the TCNQ salt, namely, the mass ratio of the ionic liquid to the TCNQ salt (ionic liquid/TCNQ salt) is preferably 1/1000 or more and less than 1/10.

(Synthesis of TCNQ Salt)

Next, synthesis of a TCNQ salt which is a constituent of an electrolyte of the present invention will be described.

1. N-n-butylisoquinolinium (TCNQ)$_2$ Salt (Also Referred to as A Salt, the Same Applies Hereinafter)

To a flask provided with a reflux condenser, commercially available n-butyl iodide (20 mmol) and isoquinoline (20 mmol) were added, followed by heating to 80° C. Since a yellow oily product would be separated from a liquid phase, heating was stopped when the product started to be generated, and the reaction was controlled to slowly progress using hot water (about 40° C.). Since the reaction would progress about 100%, the reaction was terminated when the whole reaction solution was turned to an oily state. When the heating was stopped, the product was immediately crystallized (solidified). The product was washed with ethyl ether and then purified by recrystallization with methanol.

The n-butylisoquinoline iodide (25 mmol) obtained by the above-described method was dissolved in 30 ml of acetonitrile under heating and TCNQ (30 mmol) was dissolved in 60 ml of acetonitrile under heating, and both solutions were mixed while being gently boiled. After mixing, the resulting mixture was heated for 1 hr under reflux to complete the reaction. After the completion of the reaction, the mixture was allowed to stand at room temperature for 1 hr and cooled at 5° C. overnight, and the generated dark purple crystal was collected by filtration. The resulting crystal was washed with a small amount of cooled acetonitrile and further washed with ethyl ether. The obtained salt had an electric conductivity of 3.4 Ωcm and a melting point of 210° C., and the yield was 80%.

2. N-Isoamylisoquinolinium (TCNQ)$_2$ Salt (Also Referred to as B Salt, the Same Applies Hereinafter)

A N-isoamylisoquinolinium (TCNQ)$_2$ salt was synthesized by the same method as that in (A salt) except that n-isoamyl iodide was used instead of n-butyl iodide. The obtained salt had an electric conductivity of 4.2 Ωcm and a melting point of 213° C., and the yield was 78%.

EXAMPLES

Example 1

1. Synthesis of Ionic Liquid

A stirrer was put in a well dried 1000 cm$^3$ two-neck flask equipped with a well dried Liebig reflux tube and the flask was replaced with nitrogen. To the flask, 9.9 g (0.15 mol) of sodium hydride, 200 ml of THF (tetrahydrofuran, the same applies hereinafter), and 3.85 g (10 wt %) of hexaoxacyclooctadecane were added and were well stirred, and then 9.9 g (0.15 mol) of imidazole was added thereto in an ice bath. The mixture was stirred for 2 hr, and then 50 g (0.15 mol) of 2-perfluorobutylmethyl iodide was added thereto. The resulting mixture was stirred at room temperature (hereinafter refers to a temperature of about 10 to 30° C., as long as specific description is not provided, and refers to about 25° C. as one aspect) for 4 hr. When the solution was confirmed to be changed into transparent, 15.9 g (0.15 mol) of ethyl bromide was added thereto at room temperature. After the completion of the addition, the resulting mixture was stirred at 120° C. for 7 hr. The tetrahydrofuran was evaporated under reduced pressure with an evaporator. Then, the liquid separation with methylene chloride was carried out, and methylene chloride was removed under reduced pressure with an evaporator. After drying, 42.21 g (yield: 73.9%) of 1-ethyl-3-perfluorobutylmethylimidazolium bromide was collected as a brown ionic solution.

Then, 7.82 g (0.02 mol) of the above-mentioned ionic liquid was put in a well dried 200 cm$^3$ separable flask. Then, a stirring bar was mounted on the flask and 3.0 g (0.02 mol) of lithium hexafluorosilicate and 300 ml of ion-exchange water were added thereto. The resulting mixture was stirred at room temperature (25° C.) for 30 min. After the liquid separation with methylene chloride, the remaining water was removed with magnesium sulfate. Methylene chloride was evaporated under reduced pressure with an evaporator. After vacuum dehydration at 60° C., 4.72 g (yield: 73.9%) of 1-ethyl-3-perfluorobutylmethylimidazolium (PF$_6^-$) (the chemical structure is shown by formula (5)) was collected as a brownish-red ionic liquid. This ionic liquid had a total yield of 54.6% and a viscosity of 6.3 P (25° C.) and was hydrophobic.

[Chemical formula 17]

Formula (5)

[Spectrum Data]: 500 MHz, 1H-NMR (DMSO-d6)

σ=1.33 (triplet, J=5 Hz, 3H), 4.21 (quarlet, J=5 Hz, 2H), 4.52 (singlet, 2H), 7.07 (doublet, J=5 Hz, 1H), 7.44 (doublet, J=5 Hz, 1H), 8.23 (singlet, 1H), 9.04 (singlet, 1H).

2. Evaluation of Oxide Film-Repairing Ability

An aluminum plate (50 mm in length, 5 mm in width, and 0.5 mm in thickness) with a purity of 99.99% was immersed in a mixture solution of 15% by mass of $HNO_3$ (15 parts by mass) and 85% by mass of $H_3PO_4$ (85 parts by mass) at 85° C. for 2 min and then washed with purified water at 25° C. Then, the aluminum plate was immersed in a 1 N ("N" means normal concentration) NaOH aqueous solution at 25° C. for 10 min for etching and then washed with purified water at 25° C. Then, the aluminum plate was immersed in acetone at 25° C., air-dried at 25° C., and stored in a desiccator.

Then, the aluminum plate was immersed in boiling water for 5 min for pretreatment of anodic oxidation. With reference to FIG. 2, by using a cell 10, the aluminum plate as an anode 12 immediately after the pretreatment was immersed to a depth of 1.0 cm in a diammonium adipate aqueous solution (1 g/L) as an electrolyte 14 so as to be perpendicular to the liquid surface. In addition, a cylindrical copper electrode (3.0 cm in height, 1.5 cm in internal diameter, and 1.0 mm in wall thickness) was used as a cathode 13 and was immersed in the electrolyte 14. Here, the anode 12 was disposed at the center of the cylindrical copper electrode as the cathode 13, and the distance between the anode 12 and the cathode 13 was about 7 mm. A constant current of 10 mA/cm² was applied between the anode 12 and the cathode 13, and then the voltage was gradually raised (over about 2 or 3 min) to 200 V and then the constant voltage of 200 V was maintained for 10 min for anodizing the surface of the aluminum plate as the anode 12 to form an oxide film (dielectric film) (formation treatment of oxide film).

Then, an anode of an aluminum plate and a cathode of a platinum plate of 4.0 cm in length, 3.0 cm in width, and 0.5 mm in thickness were used, and a voltage of 100 V was applied between the anode and the cathode in boiling water for 3 min. On this occasion, the aluminum plate provided with an oxide film was immersed to a depth of 1.0 cm so as to be perpendicular to the surface of the boiling water and the platinum was immersed to a depth of 2.0 cm so as to be perpendicular to the surface of the boiling water, and the distance between the anode (aluminum plate) and the cathode (platinum plate) was 1.5 cm. With this treatment, a part of the oxide film formed on the surface of the aluminum plate was broken and a defect occurred (partial breakage treatment of oxide film).

Then, with reference to FIG. 2, by using the cell 20, the aluminum plate having the oxide film with the defect was used as an anode 12 and was immersed to a depth of 0.5 cm in an electrolyte 14 of the ionic liquid (1-ethyl-3-perfluorobutylmethylimidazolium ($PF_6^-$)) prepared in this Example at 25° C. so as to be perpendicular to the liquid surface. In addition, a cylindrical copper electrode (3.0 cm in height, 1.5 cm in internal diameter, and 1.0 mm in wall thickness) was used as a cathode 13 and was immersed in the electrolyte 14. Here, as in the formation treatment of oxide film, the anode 12 was disposed at the center of the cylindrical copper electrode as the cathode 13, and the distance between the anode 12 and the cathode 13 was about 7 mm. Then, changes in the current when the voltage applied between the anode 12 and the cathode 13 was gradually raised from 0 V to 200 V at a rate of 1 V/sec were measured to obtain a current-voltage curve as shown in FIG. 1 (measurement of oxide film-forming ability and withstand voltage). The ionic liquid in this Example was hydrophobic and the initial peak voltage (the voltage at (A) point, the same applies hereinafter) was 15 V, the repair complete voltage (the voltage at (B) point, the same applies hereinafter) was 40 to 50 V, and the withstand voltage (the voltage at (C) point, the same applies hereinafter) was 180 V.

The results are shown in Table 1. In Table 1, the blank spaces (shown as "-") mean that clear voltage values have not been observed.

Voltages and currents in the evaluation of the above-mentioned oxide film-repairing ability were measured with Potentiostat/Galvanostat HA-3001A, Function Generator HB-104 manufactured by Hokuto Denko and Graphic Tachologer manufactured by Graphtec.

Example 2

1. Synthesis of Ionic Liquid

As in Example 1 except that 2-perfluorobutylethyl iodide was used instead of 2-perfluorobutylmethyl iodide, 1-ethyl-3-perfluorobutylethylimidazolium ($PF_6^-$) (the chemical structure is shown by formula (6)) was collected as an ionic liquid. This ionic liquid had a total yield of 61.6% and a viscosity of 6.4 P (25° C.) and was hydrophobic.

[Chemical formula 18]

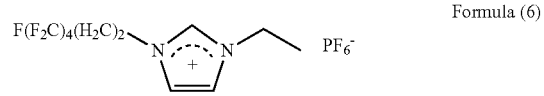

Formula (6)

[Spectrum Data]: 500 MHz, 1H-NMR (DMSO-d6)
σ=1.35 (triplet, J=5 Hz, 3H), 4.19 (quartet, J=5 Hz, 2H), 4.98 (triplet, J=5 Hz, 2H), 5.23 (triplet, J=5 Hz, 2H), 7.15 (doublet, J=5 Hz, 1H), 7.45 (doublet, J=5 Hz, 1H), 8.45 (singlet, 1H).

2. Evaluation of Oxide Film-Repairing Ability

A current-voltage curve was obtained as in Example 1 by using the ionic liquid (1-ethyl-3-perfluorobutylethylimidazolium ($PF_6^-$)) in this Example as the chemical solution 14 in the measurement of the above-mentioned oxide film-repairing ability and withstand voltage. The ionic liquid in this Example was hydrophobic. The initial peak voltage was 15 V, the repair complete voltage was 40 to 50 V, and the withstand voltage was 170 V. The results are shown in Table 1.

Example 3

1. Synthesis of Ionic Liquid

As in Example 1 except that methyl bromide was used instead of ethyl bromide, 1-methyl-3-perfluorobutylmethylimidazolium ($PF_6^-$) (the chemical structure is shown by formula (7)) was collected as an ionic liquid. This ionic liquid had a total yield of 71.6% and a viscosity of 5.9 P (25° C.) and was hydrophobic.

[Chemical formula 19]

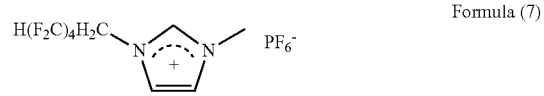

Formula (7)

[Spectrum Data]: 500 MHz, 1H-NMR (DMSO-d6)
σ=1.68 (singlet, 3H), 4.58 (singlet, 2H), 7.18 (doublet, J=5 Hz, 1H), 7.44 (doublet, J=5 Hz, 1H), 8.23 (singlet, 1H), 9.08 (singlet, 1H).

2. Evaluation of Oxide Film-Repairing Ability

A current-voltage curve was obtained as in Example 1 by using the ionic liquid (1-methyl-3-perfluorobutylmethylimidazolium ($PF_6^-$)) in this Example as the chemical solution 14 in the measurement of the above-mentioned oxide film-repairing ability and withstand voltage. The ionic liquid in this Example was hydrophobic. The initial peak voltage was 15 V, the repair complete voltage was 40 to 50 V, and the withstand voltage was 185 V. The results are shown in Table 1.

Example 4

1. Synthesis of Ionic Liquid

To a well dried 500 cm³ separable flask equipped with a stirring bar and a well dried Liebig reflux tube, 50.0 g (0.13 mol) of 2-perfluorobutylethyl iodide and 200 cm³ of toluene were added and well stirred. Then, 11.0 g (0.13 mol) of methylimidazolium was quickly added to the separable flask, and after the completion of the addition, the mixture was stirred at 120° C. for 36 hr. After the liquid separation with ether, toluene was evaporated under reduced pressure with an evaporator. After vacuum dehydration at 60° C., 42.1 g (yield: 71.0%) of 1-methyl-3-perfluorobutylethylimidazolium (I⁻) was collected as a blackish brown ionic liquid.

Then, 42.1 g of the above-mentioned ionic liquid was put in a well dried 500 cm³ separable flask. Then, a stirring bar was mounted on the flask and 14.4 g (0.09 mol) of lithium hexafluorosilicate and 300 ml of ion-exchange water were added thereto. The resulting mixture was stirred at room temperature (25° C.) for 30 min. After liquid separation with methylene chloride, the remaining water was removed with magnesium sulfate. Methylene chloride was evaporated under reduced pressure with an evaporator. After vacuum dehydration at 60° C., 19.2 g (yield: 40.8%) of 1-methyl-3-perfluorobutylethylimidazolium ($PF_6^-$) (the chemical structure is shown by formula (8)) was collected as a brownish-red ionic liquid. This ionic liquid had a total yield of 29.3% and a viscosity of 6.2 P (25° C.) and was hydrophobic.

[Chemical formula 20]

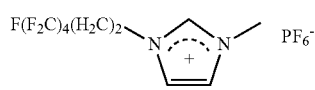

Formula (8)

[Spectrum Data]: 500 MHz, 1H-NMR (DMSO-d6)

σ=1.36 (triplet, J=5 Hz, 3H), 5.01 (triplet, J=5 Hz, 2H), 5.24 (triplet, J=5 Hz, 2H), 7.16 (doublet, J=5 Hz, 1H), 7.48 (doublet, J=5 Hz, 1H), 8.41 (singlet, 1H).

2. Evaluation of Oxide Film-Repairing Ability

A current-voltage curve was obtained as in Example 1 by using the ionic liquid (1-methyl-3-perfluorobutylethylimidazolium ($PF_6^-$)) in this Example as the chemical solution 14 in the measurement of the above-mentioned oxide film-repairing ability and withstand voltage. The ionic liquid in this Example was hydrophobic. The initial peak voltage was 15 V, the repair complete voltage was 40 to 50 V, and the withstand voltage was 170 V. The results are shown in Table 1.

Example 5

1. Synthesis of Ionic Liquid

As in Example 4 except that 2-perfluorobutyl iodide was used instead of 2-perfluorobutylethyl iodide, 1-methyl-3-perfluorobutylimidazolium ($PF_6^-$) (the chemical structure is shown by formula (9)) was collected as an ionic liquid. This ionic liquid had a total yield of 52.3% and a viscosity of 5.5 P (25° C.) and was hydrophobic.

[Chemical formula 21]

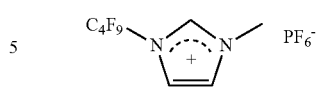

Formula (9)

[Spectrum Data]: 500 MHz, 1H-NMR (DMSO-d6)

σ=1.68 (singlet, 3H), 7.18 (doublet, J=5 Hz, 1H), 7.44 (doublet, J=5 Hz, 1H), 8.23 (singlet, 1H).

2. Evaluation of Oxide Film-Repairing Ability

A current-voltage curve was obtained as in Example 1 by using the ionic liquid (1-methyl-3-perfluorobutylimidazolium ($PF_6^-$)) in this Example as the chemical solution 14 in the measurement of the above-mentioned oxide film-repairing ability and withstand voltage. The ionic liquid in this Example was hydrophobic. The initial peak voltage was 20 V, the repair complete voltage was 50 to 60 V, and the withstand voltage was 140 V. The results are shown in Table 1, Example 6

1. Synthesis of Ionic Liquid

As in Example 4 except that lithium bis(trifluoromethane)sulfonimide was used instead of lithium hexafluorosilicate, 1-methyl-3-perfluorobutylethylimidazolium (($CF_3SO_2)_2N^-$) (the chemical structure is shown by formula (10)) was collected as an ionic liquid. This ionic liquid had a total yield of 68.3% and a viscosity of 5.8 P (25° C.) and was hydrophobic.

[Chemical formula 22]

Formula (10)

[Spectrum Data]: 500 MHz, 1H-NMR (DMSO-d6)

σ=1.32 (triplet, J=5 Hz, 3H), 4.98 (triplet, J=5 Hz, 2H), 5.20 (triplet, J=5 Hz, 2H), 7.14 (doublet, J=5 Hz, 1H), 7.45 (doublet, J=5 Hz, 1H), 8.37 (singlet, 1H).

2. Evaluation of Oxide Film-Repairing Ability

A current-voltage curve was obtained as in Example 1 by using the ionic liquid (1-methyl-3-perfluorobutylethylimidazolium (($CF_3SO_2)_2N^-$)) in this Example as the chemical solution 14 in the measurement of the above-mentioned oxide film-repairing ability and withstand voltage. The ionic liquid in this Example was hydrophobic. The initial peak voltage was 20 V, the repair complete voltage was 40 to 50 V, and the withstand voltage was 150 V. The results are shown in Table 1.

Example 7

1. Synthesis of Ionic Liquid

A stirrer was put in a well dried 1000 cm³ two-neck flask equipped with a well dried Liebig reflux tube and the flask was replaced with nitrogen. To the flask, 1.8 g (0.045 mol) of sodium hydride, 100 ml of THF, and 0.70 g (10 wt %) of hexaoxacyclooctadecane were added and were well stirred, and then 3.0 g (0.045 mol) of imidazole was added thereto in an ice bath. The mixture was stirred for 2 hr, and then 15.4 g (0.045 mol) of 2-perfluorobutylmethyl iodide was added thereto. The resulting mixture was stirred at room temperature for 4 hr. When the solution was confirmed to be changed into transparent, THF was evaporated under reduced pressure with an evaporator. Then, the liquid separation with methylene chloride was carried out, and methylene chloride was evaporated under reduced pressure with an evaporator. After drying, 10.61 g (yield: 75.8%) of 3-perfluorobutylmethylimidazole was collected as a brown ionic solution.

Then, 10.0 g (0.03 mol) of the above-mentioned ionic liquid was put in a dried 200 ml round-bottom flask. Then, 20 ml of DMF (dimethylformamide, the same applies hereinafter) was added thereto, and the mixture was well stirred. Then, 5.58 g (0.03 mmol) of methyl p-toluenesulfonate was quickly added to the flask under ice cooling. After the completion of the addition, the mixture was further stirred for 23 hr. This reaction solution was dropped into 200 ml of iced ether. The ether was removed by decantation to obtain 9.5 g (67.6%) of 1-methyl-3-perfluorobutylmethylimidazolium (p-CH$_3$—C$_6$H$_4$SO$_3^-$) (the chemical structure is shown by formula (11)) as an ionic liquid. This ionic liquid had a viscosity of 8.7 P (25° C.) and was hydrophobic.

[Chemical formula 23]

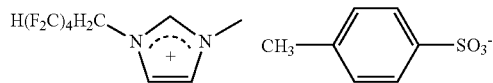

Formula (11)

[Spectrum Data]: 500 MHz, 1H-NMR (DMSO-d6)
σ=1.68 (singlet, 3H), 2.23 (singlet, 3H), 4.58 (singlet, 2H), 7.07 (doublet, J=5 Hz, 2H), 7.18 (doublet, J=5 Hz, 1H), 7.38 (doublet, J=5 Hz, 1H), 7.44 (doublet, J=5 Hz, 2H), 8.23 (singlet, 1H), 9.08 (singlet, 1H).

2. Evaluation of Oxide Film-Repairing Ability

A current-voltage curve was obtained as in Example 1 using the ionic liquid (1-methyl-3-perfluorobutylmethylimidazolium (p-CH$_3$—C$_6$H$_4$SO$_3^-$)) in this Example as the chemical solution 14 in the measurement of the above-mentioned oxide film-repairing ability and withstand voltage. The ionic liquid in this Example was hydrophobic. The initial peak voltage was 15 V, the repair complete voltage was 40 to 50 V, and the withstand voltage was 170 V. The results are shown in Table 1.

Example 8

1. Synthesis of Ionic Liquid

A stirrer was put in a well dried 300 ml round-bottom flask. To the flask, 6.4 ml (0.046 mol) of triethylamine, 5.75 g (0.046 mol) of bromoethanol, and 100 ml of THF were added and well stirred in an ice bath. To a well dried 100 ml dropping funnel, 16.77 g (0.046 mo) of dodecafluorohexanoyl chloride (C$_7$HClF$_{12}$O) and 50 ml of THF were weighed and were slowly dropped to the round-bottom flask over 1 hr in an ice bath. Then, the reaction was continued by stirring at room temperature for 67 hr. After removing THF with an evaporator, the reaction mixture was washed with excess ether and distilled water. The ether layer was collected and was removed with an evaporator, and the residual material was dried under vacuum to collect 18.2 g (yield: 87.5%) of a brown liquid. A stirrer and 15.0 g (0.033 mol) of this brown liquid were put into a dried 300 ml round-bottom flask, and 2.71 g (0.033 mol) of N-ethylimidazole and 50 ml of acetonitrile were added thereto. The mixture was well stirred in an ice bath. The reaction was further carried out at room temperature for 70 hr. After the removing of acetonitrile with an evaporator, the reaction composite was slowly dropped to 300 ml of well-cooled ether in a 500 ml beaker. With the dropping, a brown liquid was precipitated. After the stirring for 30 min, the ether layer of the supernatant was removed by decantation, and then 200 ml of ether was further added to the beaker and the mixture was stirred. Ether was removed by decantation again, and the residual material was dried to collect 14.2 g (yield: 80.2%) of a brown liquid.

Then, 13.0 g (0.024 mol) of the above-mentioned brown liquid was put in a well dried 500 cm$^3$ separable flask. Then, a stirring bar was mounted on the flask. Then, 6.9 g (0.024 mol) of lithium bis(trifluoromethane)sulfonimide and 100 ml of ion-exchange water were added thereto, and the mixture was stirred at room temperature (25° C.) for 10 hr. After the liquid separation with methylene chloride, the residual water was removed with magnesium sulfate and then methylene chloride was evaporated under reduced pressure with an evaporator. The residual material was dried under vacuum at 60° C. to collect 12.4 g (yield: 70.4%) of a brownish-red ionic liquid (the chemical structure is shown by formula (12)). This ionic liquid had a viscosity of 7.3 P (25° C.) and was hydrophobic.

[Chemical formula 24]

Formula (12)

[Spectrum Data]: 500 MHz, 1H-NMR (DMSO-d6)
σ=1.35 (triplet, J=5 Hz, 3H), 4.19 (quarlet, J=5 Hz, 2H), 4.98 (triplet, J=5 Hz, 2H), 5.23 (triplet, J=5 Hz, 2H), 7.15 (doublet, J=5 Hz, 1H), 7.45 (doublet, J=5 Hz, 1H), 8.45 (singlet, 1H), 9.34 (singlet, 1H).

2. Evaluation of Oxide Film-Repairing Ability

A current-voltage curve was obtained as in Example 1 using the ionic liquid in this Example as the chemical solution 14 in the measurement of the above-mentioned oxide film-repairing ability and withstand voltage. The ionic liquid in this Example was hydrophobic. The initial peak voltage ((A) point) was 25 V, the repair complete voltage ((B) point) was 50 to 60 V, and the withstand voltage ((C) point) was 170 V. The results are shown in Table 1.

Example 9

1. Synthesis of Ionic Liquid

A stirrer was put in a well dried 300 ml round-bottom flask. To the flask, 6.4 ml (0.046 mol) of triethylamine, 10.68 g (0.046 mol) of octafluoropentanol, and 100 ml of THF were added and well stirred in an ice bath. To a well dried 100 ml dropping funnel, 7.89 g (0.046 mo) of 3-bromopropyl chloride and 50 ml of THF were weighed and were slowly dropped to the round-bottom flask over 1 hr in an ice bath. Then, the reaction was continued by stirring at room temperature for 71 hr. After removing THF with an evaporator, the reaction mixture was washed with excess ether and distilled water. The ether layer was collected and removed with an evaporator, and the residual material was dried under vacuum to collect 12.1 g (yield: 71.7%) of a brown liquid. A stirrer and 15.0 g (0.04 mol) of this brown liquid were put into a dried 300 ml round-bottom flask, and 3.61 g (0.04 mol) of N-ethylimidazole and 50 ml of acetonitrile were added thereto. The mixture was well stirred in an ice bath. The reaction was further carried out at room temperature for 70 hr. After the removing of acetonitrile with an evaporator, the reaction composite was slowly dropped to 300 ml of well-cooled ether in a 500 ml beaker. With the dropping, a brown liquid was precipitated. After the stirring for 30 min, the ether layer of the supernatant was removed by decantation, and then 200 ml of ether was further added to the beaker and the mixture was stirred. Ether was removed by decantation again, and the residual material was dried to collect 14.1 g (yield: 75.8%) of a brown liquid. Then, 14.0 g (0.03 mol) of this brown liquid was put in a well dried 500 cm³ separable flask equipped with a stirring bar. Then, 10.79 g (0.03 mol) of lithium bis(trifluoromethane)sulfonimide and 100 ml of ion-exchange water were added thereto, and the mixture was stirred at room temperature (25° C.) for 10 hr. After the liquid separation with methylene chloride, the residual water was removed with magnesium sulfate and then methylene chloride was evaporated under reduced pressure with an evaporator. The residual material was dried under vacuum at 60° C. to collect 13.1 g (yield: 68.1%) of a brownish-red ionic liquid (the chemical structure is shown by formula (13)). This ionic liquid had a viscosity of 6.9 P (25° C.) and was hydrophobic.

[Chemical formula 25]

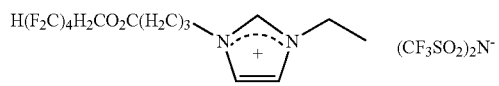

Formula (13)

[Spectrum Data]: 500 MHz, 1H-NMR (DMSO-d6)

σ=1.35 (triplet, J=5 Hz, 3H), 4.19 (quarlet, J=5 Hz, 2H), 4.98 (triplet, J=5 Hz, 2H), 5.23 (triplet, J=5 Hz, 2H), 7.15 (doublet, J=5 Hz, 1H), 7.45 (doublet, J=5 Hz, 1H), 8.45 (singlet, 1H), 9.34 (singlet, 1H).

2. Evaluation of Oxide Film-Repairing Ability

A current-voltage curve was obtained as in Example 1 using the ionic liquid in this Example as the chemical solution 14 in the measurement of the above-mentioned oxide film-repairing ability and withstand voltage. The ionic liquid in this Example was hydrophobic. The initial peak voltage was 25 V, the repair complete voltage was 50 to 60 V, and the withstand voltage was 180 V. The results are shown in Table 1.

Example 10

1. Synthesis of Ionic Liquid

To a well dried 500 cm³ separable flask equipped with a stirring bar and a Liebig reflux tube, 50.0 g (0.13 mol) of 2-perfluorobutylethyl iodide and 200 cm³ of toluene were added and were well stirred. Then, 11.0 g (0.13 mol) of methylimidazolium was quickly added to the separable flask, and after the completion of the addition, the mixture was stirred at 120° C. for 36 hr. After the liquid separation with ether, toluene was evaporated under reduced pressure with an evaporator. After vacuum dehydration at 60° C., 42.1 g (yield: 71.0%) of 1-methyl-3-perfluorobutylethylimidazolium (I⁻) was obtained as a blackish brown ionic liquid. Then, 40.0 g (0.09 mol) of the above-obtained ionic liquid was put in a well dried 500 cm³ separable flask. Then, a stirring bar was mounted on the flask, and 30.0 g (0.09 mol) of ammonium 2,2,3,3,4,4,5,5-octafluoropentanesulfate and 200 cm³ of acetone were quickly added to the above-mentioned separable flask. After the completion of the addition, the resulting mixture was stirred at room temperature (25° C.) for 12 hr.

Precipitated ammonium bromide was removed by filtration (Celite). Then, acetone in the collected acetone solution was evaporated under reduced pressure with an evaporator. After washing and concentration with methylene chloride, decolorization with activated charcoal and alumina was carried out. The activated charcoal and alumina were removed by filtration (Celite). Methylene chloride in the collected solution was evaporated under reduced pressure with an evaporator to collect 43.5 g (yield: 74.1%) of 1-methyl-3-perfluorobutylethylimidazolium=2,2,3,3,4,4,5,5,-octafluoropentanesulfate (the chemical structure is shown by formula (14)) as a light brown ionic liquid. This ionic liquid had a viscosity of 7.5 P (25° C.) and was hydrophobic.

[Chemical formula 26]

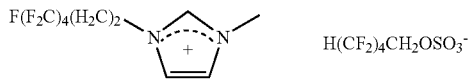

Formula (14)

[Spectrum Data]: 500 MHz, 1H-NMR (DMSO-d6)

σ=1.36 (triplet, J=5 Hz, 3H), 5.01 (triplet, J=5 Hz, 2H), 5.24 (triplet, J=5 Hz, 2H), 6.21 (singlet, 2H), 6.33 (singlet, 1H), 7.16 (doublet, J=5 Hz, 1H), 7.48 (doublet, J=5 Hz, 1H), 8.41 (singlet, 1H).

2. Evaluation of Oxide Film-Repairing Ability

A current-voltage curve was obtained as in Example 1 using the ionic liquid in this Example as the chemical solution 14 in the measurement of the above-mentioned oxide film-repairing ability and withstand voltage. The ionic liquid in this Example was hydrophobic. The initial peak voltage was 15 V, the repair complete voltage was 40 to 50 V, and the withstand voltage was 195 V. The results are shown in Table 1.

Example 11

1. Synthesis of Ionic Liquid

A stirrer was put in a well dried 1000 cm³ two-neck flask equipped with a well dried Liebig reflux tube and the flask was replaced with nitrogen. To the flask, 9.9 g (0.15 mol) of sodium hydride, 200 ml of tetrahydrofuran, and 3.85 g (10% by mass) of hexaoxacyclooctadecane were added and were well stirred, and then 9.9 g (0.15 mol) of imidazole was added thereto in an ice bath. The mixture was stirred for 2 hr, and then 50 g (0.15 mol) of 2-perfluorobutylethyl iodide was added thereto. The resulting mixture was stirred at room temperature for 4 hr. When the solution was confirmed to be changed into transparent, 15.9 g (0.15 mol) of ethyl bromide was added thereto at room temperature. After the completion of the addition, the resulting mixture was stirred at 120° C. for 7 hr. The tetrahydrofuran was evaporated under reduced pressure with an evaporator. After the liquid separation with methylene chloride, methylene chloride was evaporated under reduced pressure with an evaporator. After drying, 42.21 g (yield: 73.9%) of 1-methyl-3-perfluorobutylethylimidazolium (Br⁻) was collected as a brown ionic solution. Then, 7.82 g (0.02 mol) of this ionic liquid, 6.56 g (0.02 mol) of ammonium 2,2,3,3,4,4,5,5-octafluoropentanesulfate, and 100 cm³ of acetone were put in a well dried 500 cm³ separable flask. Then, a stirring bar and Liebig reflux tube were mounted on the flask and the resulting mixture was stirred at room temperature (25° C.) for 12 hr. The precipitated ammonium chloride was removed by filtration (Celite). Acetone in the collected acetone solution was evaporated under reduced pressure with an evaporator. The residual material was washed and concentrated with a mixture solution of n-hexane/ethyl acetate (volume ratio: 3/1) and was dissolved in acetone again and decolorized with activated charcoal. Then, acetone in the collected acetone solution was evaporated under reduced pressure with an evaporator again to obtain 9.82 g (yield: 78.3%) of 1-methyl-3-perfluorobutylethylimidazolium=2,2,3,3,4,4,5,5,-octafluoropentanesulfate (the chemical structure is shown by formula (14)) as a light brown ionic liquid. This ionic liquid had a viscosity of 6.8 P (25° C.) and was hydrophobic.

[Chemical formula 27]

Formula (14)

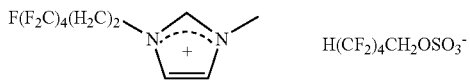

[Spectrum Data]: 500 MHz, 1H-NMR (DMSO-d6)

σ=1.38 (triplet, J=5 Hz, 3H), 5.01 (triplet, J=5 Hz, 2H), 5.15 (triplet, J=5 Hz, 2H), 6.20 (singlet, 2H), 6.33 (singlet, 1H), 7.13 (doublet, J=5 Hz, 1H), 7.55 (doublet, J=5 Hz, 1H), 8.42 (singlet, 1H).

2. Evaluation of Oxide Film-Repairing Ability

A current-voltage curve was obtained as in Example 1 using the ionic liquid in this Example as the chemical solution 14 in the measurement of the above-mentioned oxide film-repairing ability and withstand voltage. The ionic liquid in this Example was hydrophobic. The initial peak voltage was 15 V, the repair complete voltage was 40 to 50 V, and the withstand voltage was 190 V. The results are shown in Table 1.

Comparative Example 1

1. Adipate Chemical Solution

As an adipate chemical solution, a 1 g/L ammonium adipate aqueous solution was used.

2. Evaluation of Oxide Film-Repairing Ability

A current-voltage curve was obtained as in Example 1 using the adipate chemical solution in this Comparative Example as the chemical solution 14 in the measurement of the above-mentioned oxide film-repairing ability and withstand voltage. The initial peak voltage was 45 V, the repair complete voltage was 120 V, and the withstand voltage was 180 V. The results are shown in Table 1.

Comparative Example 2

1. Oxalic Acid Chemical Solution

As an oxalic acid chemical solution, a 2% by mass oxalic acid aqueous solution was used.

2. Evaluation of Oxide Film-Repairing Ability

A current-voltage curve was obtained as in Example 1 using the oxalic acid chemical solution in this Comparative Example as the chemical solution 14 in the measurement of the above-mentioned oxide film-repairing ability and withstand voltage. The initial peak voltage and the repair complete voltage were not observed, and the withstand voltage was 147 V. The results are shown in Table 1.

Comparative Example 3

1. Ionic Liquid

As an ionic liquid, 1-ethyl-3-methylimidazolium (p-$CH_3$—$C_6H_4SO_3^-$) (manufactured by Strem) was used. This ionic liquid was hydrophilic.

2. Evaluation of Oxide Film-Repairing Ability

A current-voltage curve was obtained as in Example 1 using the ionic liquid in this Comparative Example as the chemical solution 14 in the measurement of the above-mentioned oxide film-repairing ability and withstand voltage. The ionic liquid of this Comparative Example was hydrophobic. The initial peak voltage ((A) point) was 15 V, the repair complete voltage ((B) point) was 40 to 50 V, and the withstand voltage ((C) point) was 90 to 100 V. The results are shown in Table 1.

Comparative Example 4

1. Ionic Liquid

As an ionic liquid, 1-ethyl-3-methylimidazolium chloride (manufactured by Kanto Chemical) was used. This ionic liquid was hydrophilic.

2. Evaluation of Oxide Film-Repairing Ability

A current-voltage curve was obtained as in Example 1 using the ionic liquid in this Comparative Example as the chemical solution 14 in the measurement of the above-mentioned oxide film-repairing ability and withstand voltage. The ionic liquid of this Comparative Example was hydrophilic, and the initial peak voltage and the repair complete voltage were not observed. The withstand voltage was less than 20 V. The results are shown in Table 1.

Comparative Example 5

1. Ionic Liquid

As an ionic liquid, 1-ethyl-3-methylimidazolium bromide (manufactured by Kanto Chemical) was used. This ionic liquid was hydrophilic.

2. Evaluation of Oxide Film-Repairing Ability

A current-voltage curve was obtained as in Example 1 using the ionic liquid in this Comparative Example as the chemical solution 14 in the measurement of the above-mentioned oxide film-repairing ability and withstand voltage. The ionic liquid of this Comparative Example was hydrophilic, and the initial peak voltage and the repair complete voltage were not observed. The withstand voltage was less than 20 V. The results are shown in Table 1.

TABLE 1

| | Evaluation of Oxide Film-Repairing Ability and Withstand Voltage | | |
|---|---|---|---|
| | Peak Voltage (A point) (V) | Repair Complete Voltage (B point) (V) | Withstand Voltage (C point) (V) |
| Example 1 | 15 | 40~50 | 180 |
| Example 2 | 15 | 40~50 | 170 |
| Example 3 | 15 | 40~50 | 185 |
| Example 4 | 15 | 40~50 | 170 |
| Example 5 | 20 | 50~60 | 140 |
| Example 6 | 20 | 40~50 | 150 |
| Example 7 | 15 | 40~50 | 170 |
| Example 8 | 25 | 50~60 | 170 |
| Example 9 | 25 | 50~60 | 180 |
| Example 10 | 15 | 40~50 | 195 |
| Example 11 | 15 | 40~50 | 190 |

TABLE 1-continued

| | Evaluation of Oxide Film-Repairing Ability and Withstand Voltage | | |
|---|---|---|---|
| | Peak Voltage (A point) (V) | Repair Complete Voltage (B point) (V) | Withstand Voltage (C point) (V) |
| Comparative Example 1 | 45 | 120 | 180 |
| Comparative Example 2 | — | — | 147 |
| Comparative Example 3 | 15 | 40~50 | 90~100 |
| Comparative Example 4 | — | — | <20 |
| Comparative Example 5 | — | — | <20 |

As shown in Table 1, in the oxide film-repairing ability evaluation experiments, though in cases of using a fluorine cation-containing ionic liquid as the electrolyte (Examples 1 to 11) the withstand voltages were the same levels of that in case of using an adipate chemical solution (Comparative Example 1), the initial peak voltages and repair complete voltages were decreased. This means that an oxide film can be repaired at a lower voltage. In other words, it is confirmed that fluorine cation-containing ionic liquids have a similar withstand voltage but higher oxide film-repairing ability compared to the adipate chemical solution.

Further, in a case of using an oxalic acid chemical solution as the electrolyte (Comparative Example 2), the initial peak voltage and the repair complete voltage were not recognized and the withstand voltage was lower than those in cases using a fluorine cation-containing ionic liquid as the electrolyte (Examples 1 to 4, and 6 to 11). Therefore, it is confirmed that the oxalic acid chemical solution is poor in oxide film-repairing ability and the withstand voltage thereof is lower than those in fluorine cation-containing ionic liquids.

Further, in cases of using an ionic liquid containing chloride ions or bromide ions as an anionic component of the electrolyte (Comparative Examples 4 and 5), the initial peak voltage and the repair complete voltage were not observed and the withstand voltages were significantly decreased. It is thought that this is caused by that the anionic components such as chloride ions or bromide ions etch the metal oxide film. Therefore, it is thought that an ionic liquid containing chloride ions or bromide ions are not appropriate for achieving the purpose of the present invention.

In addition, an ionic liquid including an anion component containing at least one anion selected from the group consisting of fluoroalkylsulfonate anions, fluorocycloalkylsulfonate anions, and fluorobenzylsulfonate anions and oxide film-repairing ability thereof will be shown below as referential examples.

Referential Example 1

1. Synthesis of Ionic Liquid

A stirrer was put in a well dried 500 ml round-bottom flask, and 35.4 g (0.27 mol) of sodium vinylsulfonate was added to 250 ml of acetonitrile, 250 ml of purified water, 22.68 g (0.27 mol) of sodium hydrogen carbonate, 47.0 g of sodium thiosulfate, and 93.4 g (0.27 mol) of 2-perfluorobutyl iodide in the flask. The mixture was stirred at room temperature (for example, at 25° C.) for 4 hr. Then, the hydrophobic by-products were removed by ether extraction, and the aqueous layer was lyophilized. The obtained brown liquid (38.2 g, 0.08 mol) was added to 5.23 g (0.08 mol) of Zn power, 1.3 g (0.01 mol) of nickel chloride, 60 ml of THF, and 20 ml of distilled water, and the resulting mixture was stirred at room temperature for 12 hr. Then, the mixture was adjusted to be acidic with concentrated sulfuric acid and was extracted with methylene chloride to isolate this sulfuric acid. After the neutralization with sodium hydroxide to obtain a sodium salt, 10.5 g (0.08 mol) of butylmethylimidazolium chloride was added thereto. The resulting mixture was stirred in acetone at room temperature for 12 hr. Acetone was evaporated under reduced pressure. After the liquid separation with methylene chloride, the evaporation under the reduced pressure was carried out for drying to obtain a brown ionic liquid (the chemical structure is shown by formula (15)). This ionic liquid had a yield of 37%, a viscosity of 8.3 P (25° C.) and was hydrophobic.

[Chemical formula 28]

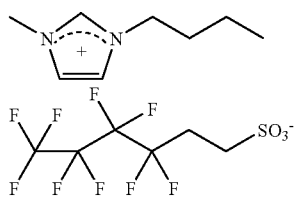

Formula (15)

[Spectrum Data]: 500 MHz, 1H-NMR (DMSO-d6)

σ=1.33 (triplet, J=5 Hz, 3H), 1.48 (triplet, J=5 Hz, 2H), 1.85 (triplet, J=5 Hz, 2H), 2.39 (triplet, J=5 Hz, 2H), 4.21 (multiplet, J=5 Hz, 4H), 7.07 (doublet, J=5 Hz, 1H), 7.44 (doublet, J=5 Hz, 1H), 8.23 (singlet, 1H), 9.33 (triplet, J=5 Hz, 2H), 9.48 (triplet, J 5 Hz, 2H).

2. Evaluation of Oxide Film-Repairing Ability

A current-voltage curve was obtained as in Example 1 using the ionic liquid in this Referential Example as the electrolyte 14 in the measurement of the above-mentioned oxide film-repairing ability and withstand voltage. The ionic liquid in this Referential Example was hydrophobic. The initial peak voltage was 20 V, the repair complete voltage was 40 to 50 V, and the withstand voltage was 170 V.

Referential Example 2

1. Ionic Liquid

A stirrer was put in a well dried 500 ml round-bottom flask, and 35.4 g (0.27 mol) of sodium vinylsulfonate was added to 250 ml of acetonitrile, 250 ml of purified water, 22.68 g (0.27 mol) of sodium hydrogen carbonate, 47.0 g of sodium thiosulfate, and 93.4 g (0.27 mol) of 2-perfluorobutyl iodide in the flask. The mixture was stirred at room temperature (for example, at 25° C.) for 4 hr. Then, the hydrophobic by-products were removed by ether extraction, and the aqueous layer was lyophilized. The obtained brown liquid (38.2 g, 0.08 mol) was added to 5.23 g (0.08 mol) of Zn power, 1.3 g (0.01 mol) of nickel chloride, 60 ml of THF, and 20 ml of distilled water, and the resulting mixture was stirred at room temperature for 12 hr. Then, the mixture was adjusted to be acidic with concentrated sulfuric acid and was extracted with methylene chloride to isolate this sulfuric acid. Then, this sulfuric acid, 8.01 g (0.08 mol) of ethylimidazole, and 50 ml of ethanol were well stirred in an ice bath and then at room temperature for 24 hr. Ethanol in the reaction mixture was removed with an evaporator, and then by-products were removed by ether extraction. The residual material was dried under vacuum to obtain a brown ionic liquid (the chemical structure is shown by formula (16)). This ionic liquid had a yield of 68%, a viscosity of 6.4 P (25° C.) and was hydrophobic.

[Chemical formula 29]

Formula (16)

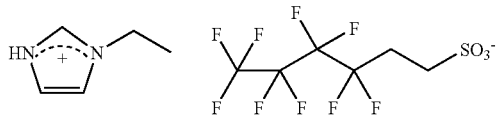

[Spectrum Data]: 500 MHz, 1H-NMR (DMSO-d6)

σ=1.33 (triplet, J=5 Hz, 3H), 1.48 (triplet, J=5 Hz, 2H), 1.85 (triplet, J=5 Hz, 2H), 2.39 (triplet, J=5 Hz, 2H), 4.21 (multiplet, J=5 Hz, 4H), 7.07 (doublet, J=5 Hz, 1H), 7.44 (doublet, J=5 Hz, 1H), 8.23 (singlet, 1H), 9.33 (triplet, J=5 Hz, 2H), 9.48 (triplet, J=5 Hz, 2H).

2. Evaluation of Oxide Film-Repairing Ability

A current-voltage curve was obtained as in Example 1 using the ionic liquid in this Referential Example as the electrolyte 14 in the measurement of the above-mentioned oxide film-repairing ability and withstand voltage. The ionic liquid in this Referential Example was hydrophobic. The initial peak voltage was 20 V, the repair complete voltage was 50 to 60 V, and the withstand voltage was 190 V.

The invention claimed is:

1. An ionic liquid comprising a cationic component and an anionic component, wherein the cationic component contains fluorine atoms and contains a chemical structure represented by formula (1) or formula (2):

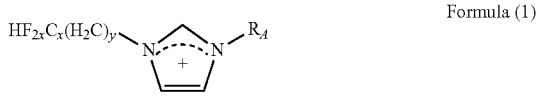

Formula (1)

(in formula (1), x denotes an integer of 1 to 20, y denotes an integer of 0 to 5, and $R_A$ denotes one selected from the group consisting of hydrogen, aliphatic hydrocarbon groups, aromatic hydrocarbon groups, carboxylic acid groups, ester groups, ether groups, acyl groups, and amino groups),

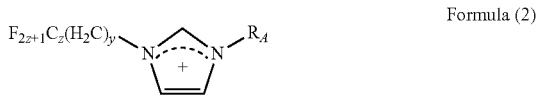

Formula (2)

(in formula (2), z denotes an integer of 2 to 20, y denotes an integer of 0 to 5, and $R_A$ denotes one selected from the group consisting of hydrogen, aliphatic hydrocarbon groups, aromatic hydrocarbon groups, carboxylic acid groups, ester groups, ether groups, acyl groups, and amino groups).

2. The ionic liquid according claim 1, wherein the anionic component contains fluorine atoms.

3. The ionic liquid according to claim 2, wherein the ratio of the number $n_u$ of hydrogen atoms to the number $n_F$ of fluorine atoms in the anionic component is $n_H:n_F$=0:100 to 60:40.

4. The ionic liquid according to claim 2, wherein the anionic component contains a chemical structure represented by formula (3) or formula (4):

Formula (3)

(in formula (3), x denotes an integer of 1 to 20, and y denotes an integer of 0 to 5),

Formula (4)

(in formula (4), z denotes an integer of 1 to 20, and y denotes an integer of 0 to 5).

5. The ionic liquid according to claim 2, wherein the anionic component contains at least one atomic group selected from the group consisting of bis(trifluoromethylsulfonyl)imide anions, $CHF_2$—$CF_2$—$CH_2OSO_3^-$ atomic groups, $CHF_2$—$(CF_2)_3$—$CH_2OSO_3^-$ atomic groups, $CF_3$—$(CF_2)_2$—$CH_2OSO_3^-$ atomic groups, and $CF_3$—$(CF_2)_6$—$CH_2OSO_3^-$ atomic groups.

6. The ionic liquid according to claim 1, wherein the anionic component contains an $R_B$—$SO_v$— atomic group (wherein v denotes an integer of 2 to 4, and $R_B$ denotes an aromatic or aliphatic compound having 1 to 50 carbon atoms).

7. The ionic liquid according to claim 1, wherein the anionic component contains a carboxyl group anion (—$COO^-$).

8. The ionic liquid according to claim 1, wherein the ionic liquid comprises a chemical structure represented by formula (5):

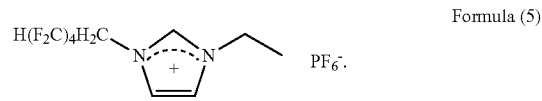

Formula (5)

9. The ionic liquid according to claim 1, wherein the ionic liquid comprises a chemical structure represented by formula (6):

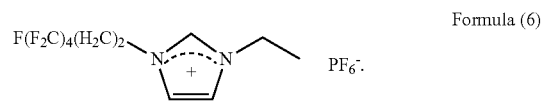

Formula (6)

10. The ionic liquid according to claim 1, wherein the ionic liquid comprises a chemical structure represented by formula (7):

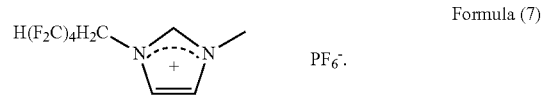

Formula (7)

11. The ionic liquid according to claim 1, wherein the ionic liquid comprises a chemical structure represented by formula (8):

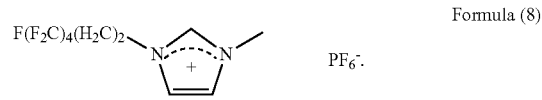

Formula (8)

12. The ionic liquid according to claim 1, wherein the ionic liquid comprises a chemical structure represented by formula (9):

Formula (9)

13. The ionic liquid according to claim 1, wherein the ionic liquid comprises a chemical structure represented by formula (10):

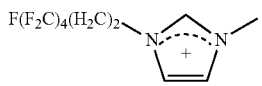

Formula (10)

14. The ionic liquid according to claim 1, wherein the ionic liquid comprises a chemical structure represented by formula (11):

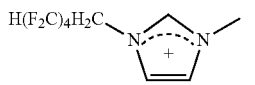 

Formula (11)

15. An ionic liquid comprising a cationic component and an anionic component, wherein the ionic liquid comprises a chemical structure represented by formula (12):

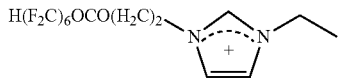

Formula (12)

16. An ionic liquid comprising a cationic component and an anionic component, wherein the ionic liquid comprises a chemical structure represented by formula (13):

Formula (13)

17. The ionic liquid according to claim 1, wherein the ionic liquid comprises a chemical structure represented by formula (14):

Formula (14)

18. The ionic liquid according to claim 1, wherein, when a defect in an oxide film formed on the surface of a metal is anodized by a two-electrode system in the presence of the ionic liquid,
a current-voltage curve obtained by applying a forward voltage from 0 V at a constant voltage rate of 1 V/s has an initial peak voltage and give a withstand voltage of 50 V or more.

19. The ionic liquid according to claim 18, wherein the withstand voltage is 100 V or more.

20. The ionic liquid according to claim 18, wherein the initial peak voltage is 30 V or less.

21. The ionic liquid according to claim 18, wherein the initial peak voltage is 15 V or less.

22. The ionic liquid according to claim 18, wherein the metal contains at least one selected from the group consisting of aluminum and/or alloys thereof, tantalum and/or alloys thereof, and niobium and/or alloys thereof.

23. A method for manufacturing the ionic liquid according to claim 1, wherein
an imidazolium derivative and a fluoroalkyl halide compound are reacted.

* * * * *

UNITED STATES PATENT AND TRADEMARK OFFICE
CERTIFICATE OF CORRECTION

PATENT NO. : 8,034,956 B2
APPLICATION NO. : 11/667541
DATED : October 11, 2011
INVENTOR(S) : Yasuhiro Tsukada et al.

It is certified that error appears in the above-identified patent and that said Letters Patent is hereby corrected as shown below:

In the Specifications:

Column 1, Line 54: Delete "ELECTROLYTE" and insert --ELECTROLYTIC--

In the Claims:

Column 41, Line 65: Delete "$n_u$" and insert --$n_H$--

Column 42, Line 16: Delete "$CH_2OSO_3'''$" and insert --$CH_2OSO_3^-$--

Column 42, Line 17: Delete "$CH_2OSO_3'''$" and insert --$CH_2OSO_3^-$--

Signed and Sealed this
Twenty-third Day of April, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,034,956 B2  
APPLICATION NO. : 11/667541  
DATED : October 11, 2011  
INVENTOR(S) : Yasuhiro Tsukada et al.

Page 1 of 1

It is certified that error appears in the above-identified patent and that said Letters Patent is hereby corrected as shown below:

Title Page, Item (54) and in the Specification at Column 1, Line 4, Title:
Delete "ELECTROLYTE" and insert --ELECTROLYTIC--

In the Claims:

Column 41, Line 65: Delete "$n_u$" and insert --$n_H$--

Column 42, Line 16: Delete "$CH_2OSO_3'$" and insert --$CH_2OSO_3^-$--

Column 42, Line 17: Delete "$CH_2OSO_3'$" and insert --$CH_2OSO_3^-$--

This certificate supersedes the Certificate of Correction issued April 23, 2013.

Signed and Sealed this  
Twenty-first Day of May, 2013

Teresa Stanek Rea  
*Acting Director of the United States Patent and Trademark Office*